(12) United States Patent
Deming

(10) Patent No.: US 6,680,365 B1
(45) Date of Patent: Jan. 20, 2004

(54) METHODS AND COMPOSITIONS FOR CONTROLLED POLYPEPTIDE SYNTHESIS

(75) Inventor: Timothy J. Deming, Summerland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/272,109

(22) Filed: Mar. 19, 1999

Related U.S. Application Data

(60) Provisional application No. 60/078,649, filed on Mar. 19, 1998, now abandoned.

(51) Int. Cl.⁷ .................................................. C07K 1/00
(52) U.S. Cl. ........................... 530/333; 530/338; 556/1; 556/45; 556/136; 556/137; 556/138
(58) Field of Search ................................. 530/350, 333, 530/338; 556/1, 45, 136, 137, 138

(56) References Cited

PUBLICATIONS

Deming, Amino Acid Derived Nickelacycles: Intermediates in Nickel–Mediated Polypeptide Synthesis J. Am. Chem. Soc. Vol 120, pp. 4240–4241, 1998.*
Yamashita, Shinsuke Macromolecules 7(4), 410–15, 1974.*
Yamashita, Shinsuke Macromolecules 7(6), 724–7, 1974.*
Deming, Timothy J. Polym. Prepr. (Am. Chem. Soc., Div. Polym. Chem.) 37(1), 435–6, 1996.*
M. Idelson, et al., *J. Am. Chem Soc.*, 80:2387–2393 (1958).
M.Idelson et al. *Laboratory of Children's Cancer Research Foundation*, 79:3948–3955 (1957).
Yamashita, S.; Tani, H. *Macromolecules*, 1974, 7, 406–409.
H. Yamamoto, *J.Am. Chem. Soc.*, 109:1092–1100 (1987).
Komiya et al., *Chemistry Letters, The Chemical Society of Japan*, 193–196 (1981).
Wanjek et al., *Chem Ber.* 121:1417–1420 (1988) In German Z. *Chem.*, 24:103104 (1984) Zur Reaktion von phosphin-haltigen Nickel(0).

T.J.Deming, *J. Am. Chem Soc.*, 120:4240–4241 (1998).
Tetsuya Makino et al., *Die Makromolekulare Chemie*, 131:147–167, (1970).
S. Freireich et al., "Polymerization of N–Carboxy Anhydrides by Organotin Catalysts" in *European Polymer Journal*, Pergamon Press, 10:439–443 (197487).
T.J. Deming, "Polypeptide Materials: New Synthetic Methods and Applications" *Adv. Materials*, 9:299–311 (1997).
T.J. Deming, "Transition Metal–Amine Initiators for Preparation of Well–Defined Poly(g–benzyl-L-glutamate)" *J. Am. Chem. Soc.*, 1997, 119:2759–2760 (1997).
E. Uhlig, et al., *Z. Anorg. Allg. Chem.*, 465:141–146 (1980).
A.M. Castaño, et al., *Organometallics*, 13:2262–2268 (1994).
T.J. Deming, *Nature*, 390:386–389 (1997).

* cited by examiner

*Primary Examiner*—Christopher S. F. Low
*Assistant Examiner*—David Lukton
(74) *Attorney, Agent, or Firm*—Fulbright & Jaworski

(57) ABSTRACT

Methods and compositions for the generation of polypeptides having varied material properties are disclosed herein. Methods include means for making block copolypeptides and related protocols for adding aminoacid-N-carboxyanhydrides (NCAs) to polyaminoacid chains by exposing the NCA to solutions containing polyaminoacid chains having an amido amidate metallacyle end groups and reacting the NCA with the amido containing metallacyle end group so that the NCA is added to the polyaminoacid chain. Addition methods include means of controlling the addition of aminoacid-N-carboxyanhydrides to polyaminoacid chains by reacting NCAs with initiator molecules and allowing initiator complexes to open the ring of the NCAs through oxidative addition across either the O—$C_5$ or O—$C_2$ anhydride bond resulting a controlled polypeptide polymerization. Novel compositions for use in peptide synthesis and design including five and six membered amido-containing metallacycles and block copolypeptides are also disclosed.

25 Claims, 6 Drawing Sheets

(1)

(2)

(3)

(4)

DIPRIM

DPIM

DMIM

DPOX

TMOX

DMOX-py

METHODS AND COMPOSITIONS FOR CONTROLLED POLYPEPTIDE SYNTHESIS

CROSS-REFERENCE TO RELATED APPLICATIONS

This application is a non-provisional application under 37 CFR 1.15(b) claiming priority under Section 119(e) to provisional application No. 60/078,649, filed Mar. 19, 1998 now abandoned, the contents of which is hereby incorporated by reference.

STATEMENT REGARDING FEDERALLY FUNDED RESEARCH

This invention was made with Government support under Grant Nos. DMR 9632716 and CHE 9701969, awarded by the National Science Foundation. The Government has certain rights in this invention.

BACKGROUND OF THE INVENTION

1. Field of the Invention

The present invention relates to the synthesis of amino-acid based polymers. In particular, this invention relates to methods and compositions for the synthesis of amino-acid based polymers using catalysts under "living" conditions, that is conditions free of termination and chain transfer.

2. Description of Related Art

Synthetic polypeptides have a number of advantages over peptides produced in biological systems and have been used to make fundamental contributions to both the physical chemistry of macromolecules and the analysis of protein structures. See e.g. G. D. Fasman, *Poly α-Amino Acids*, Dekker, N.Y., (1967). Moreover, synthetic peptides are both more cost efficient and can possess a greater range of material properties than peptides produced in biological systems.

Small synthetic peptide sequences, typically less than 100 residues in length, are conventionally prepared using stepwise solid-phase synthesis. Such solid phase synthesis makes use of an insoluble resin support for a growing oligomer. A sequence of subunits, destined to comprise a desired polymer, are reacted together in sequence on the support. A terminal amino acid is attached to the solid support in an initial reaction, either directly or through a keying agent. The terminal residue is reacted, in sequence, with a series of further residues such as amino acids or blocked amino acid moieties to yield a growing oligomer attached to the solid support through the terminal residue. At each stage in the synthetic scheme, unreacted reactant materials are washed out or otherwise removed from contact with the solid phase. The cycle is continued with a pre-selected sequence of residues until the desired polymer has been completely synthesized, but remains attached to the solid support. The polymer is then cleaved from the solid support and purified for use. The foregoing general synthetic scheme was developed by R. B. Merrifield for use in the preparation of certain peptides. See e.g. See Merrifield's Nobel Prize Lecture "Solid Phase Synthesis", *Science*, Volume 232, pp. 341–347 (1986).

A major disadvantage of conventional solid phase synthetic methods for the preparation of oligomeric materials results from the fact that the reactions involved in the scheme are imperfect; no reaction proceeds to 100% completion. As each new subunit is added to the growing oligomeric chain a small, but measurable, proportion of the desired reaction fails to take place. The result of this is a series of peptides, nucleotides, or other oligomers having deletions in their sequence. The result of the foregoing imperfection in the synthetic scheme is that as desired chain length increases, the effective yield of desired product decreases drastically, since increased chances for deletion occur. Similar considerations attend other types of unwanted reactions, such as those resulting from imperfect blocking, side reactions, and the like. Of equal, if not greater, significance, is the fact that the increasing numbers of undesired polymeric species which result from the failed individual reactions produce grave difficulties in purification. For example, if a polypeptide is desired having 100 amino acid residues, there may be as many as 99 separate peptides having one deleted amino acid residue and an even greater possible number of undesired polymers having two or more deleted residues, side reaction products and the like.

Due to the above-mentioned problems associated with solid phase methodologies, practitioners employ other protocols for peptide synthesis. For example, synthetic copolymers of narrow molecular weight distribution, controlled molecular weight, and with block and star architectures can be prepared using so called living polymerization techniques. See e.g. O. Webster, *Science*, 251:887–893 (1991). In these polymerizations, chains grow linearly by consecutive addition of monomers, and chain-breaking transfer and termination reactions are absent. The active end-groups of growing polymer chains do not deactivate (i.e. they remain "living") and chains continue to grow as long as monomer is present. Chain length in living polymerizations is controlled through adjustment of monomer to initiator stoichiometry. Under circumstances when all chains grow at the same rate, living polymers will possess a narrow distribution of chain lengths. Complex sequences, such as block copolymers, are then built up by stepwise addition of different monomers to the growing chains. A. Noshay, et al., *Block Copolymers*, Academic Press, New York, (1977).

The chemical synthesis of high molecular weight polypeptides is most directly accomplished by the ring-opening polymerization of α-aminoacid-N-carboxyanhydride (NCA) monomers (see equation 1 below). See e.g. H. R. Kricheldorf, in *Models of Biopolymers by Ring-Opening Polymerization*, Penczek, S. Ed., CRC Press, Boca Raton, (1990). In general terms, NCA polymerizations can be classified into two categories based on the type of initiator used: either a nucleophile (typically a primary amine) or strong base (typically a sodium alkoxide) (see equation 1 below). Nucleophile initiated polymerizations are believed to propagate through a primary amine end-group (see equation 2 below). These polymerizations display complicated kinetics where an initial slow first order process is followed by accelerated monomer consumption: indicative of multiple propagating species with different reactivities. See e.g. M. Idelson, et al., *J. Am. Chem Soc.*, 80:2387–2393 (1958). The prevalence of side reactions limit these initiators to the formation of low molecular weight polymers (10 kDa<$M_n$<50 kDa) which typically contain a substantial fraction of molecules with degree of polymerization less than 10. As such, the polymers have very broad molecular weight distributions ($M_w/M_n$=4–10). See e.g. R. D. Lundberg, et al., *J. Am. Chem Soc.*, 79:3961–3972 (1957).

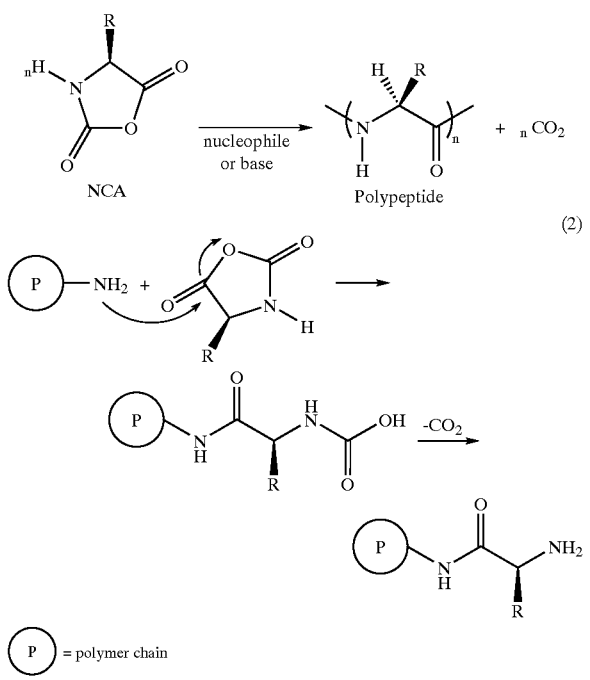

(P) = polymer chain

Strong base initiated NCA polymerizations are much faster than amine initiated reactions. These polymerizations are poorly understood but are believed to propagate through either NCA anion or carbamate reactive species (see equations 3 and 4 below, respectively). See e.g. C. H. Bamford, et al., *Synthetic Polypeptides*, Academic Press, New York, (1956).

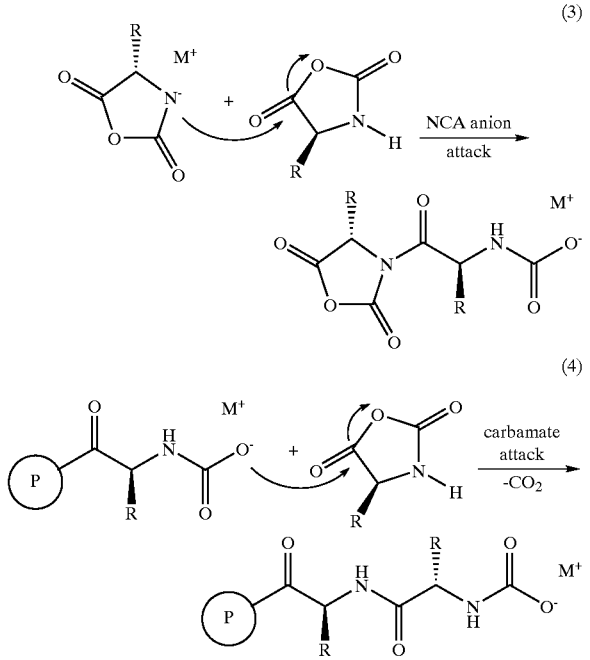

A significant limitation of NCA polymerizations employing conventional initiators is due to the fact that they are plagued by chain-breaking transfer and termination reactions which prevent formation of block copolymers. See e.g. H. R. Kricheldorf, α-*Aminoacid-N-Carboxyanhydrides and Related Materials*, Springer-Verlag, New York, (1987). Consequently, the mechanisms of NCA polymerization have been under intensive study so that problematic side reactions could be eliminated. See e.g. H. R. Kricheldorf, in *Models of Biopolymers by Ring-Opening Polymerization*, Penczek, S. Ed., CRC Press, Boca Raton, (1990). These investigations have been severely hindered by the complexity of the polymerizations, which can proceed through multiple pathways. Moreover, the high sensitivity of NCA polymerizations to reaction conditions and impurities has also led to contradictory data in the literature resulting in controversy over the different hypothetical mechanisms. H. Sekiguchi, *Pure and Appl. Chem.*, 3:1689–1714 (1981); H. Sekiguchi, et al., *J. Poly. Sci. Symp.*, 52:157–171(1975).

The significant problems with existing peptide synthesis methodologies create a variety of problems for practitioners. For example, the chain breaking transfer reactions that occur in the NCA polymerizations preclude the systematic control of peptide molecular weight. Moreover, block copolymers cannot be prepared using such methods. Consequently, there is a need for novel methods and compositions which allow for the facile generation of peptides tailored to have specific desirable-properties.

SUMMARY OF THE INVENTION

The present invention discloses novel methods and compositions which address the need for advanced tools to generate polypeptides having varied material properties. The methods and initiator compositions for NCA polymerization disclosed herein allow the precise control of such polypeptide synthesis. In particular, the methods of the invention allow successful peptide synthesis by utilizing the versatile chemistry of transition metals to mediate the addition of monomers to the active polymer chain-ends, and therefore eliminate chain-breaking side reactions in favor of the chain-growth process. In this way, the disclosed methods allow the formation of block copolymers. Moreover, by binding the active end-group of the growing polymer to a metal center, its reactivity toward monomers can be precisely controlled through variation of the metal and ancillary ligands bound to the metal. The wide range of selective chemical transformations and polymerizations which are catalyzed by transition metal complexes attests to the versatility of this approach.

One embodiment of the invention provides a method of making a block copolypeptide consisting of combining an amount of a first aminoacid-N-carboxyanhydride (NCA) monomer with an initiator molecule comprising a low valent transition metal-Lewis Base ligand complex so that a polyaminoacid chain is generated and then combining an amount of a second aminoacid-N-carboxyanhydride monomer with the polyaminoacid chain so that the second aminoacid-N-carboxyanhydride monomer is added to the polyaminoacid chain. In a preferred embodiment of this method, the initiator molecule combines with the first aminoacid-N-carboxyanhydride monomer to form an amido containing metallacycle intermediate of the general formulae:

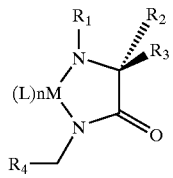

wherein
- M is the low valent transition metal;
- L is the Lewis Base ligand; each of R1, R2 and R3 independently is a moiety selected from the group consisting of the side chains of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine; and
- R4 is the polyaminoacid chain.

A related embodiment of the invention consists of a method of adding an aminoacid-N-carboxyanhydride (NCA) to a polyaminoacid chain having an amido containing metallacycle end group by combining the NCA with the polyaminoacid chain so that the NCA is added to the polyaminoacid chain.

Another embodiment of the invention disclosed herein entails a method of polymerizing aminoacid-N-carboxyanhydride monomers by combining a NCA monomer with an initiator molecule complex comprised of a low valent transition metal-Lewis Base ligand. A specific embodiment of the invention disclosed herein entails a method of polymerizing aminoacid-N-carboxyanhydride monomers having a ring with a $O-C_5$ and a $O-C_2$ anhydride bond which consists of combining a first NCA monomer with an initiator molecule complex comprised of a low valent metal capable of undergoing an oxidative addition reaction wherein the oxidative addition reaction formally increases the oxidation state by two electrons; and an electron donor comprising a Lewis base, and then allowing the initiator molecule to open the ring of the first NCA through oxidative addition across either the $O-C_5$ or $O-C_2$ anhydride bond and then combine with a second NCA monomer, to form an amido-containing metallacycle and then allowing a third NCA monomer to combine with the amido containing metallacyle so that the amido nitrogen of the amido containing metallacyle attacks the carbonyl carbon of the NCA and the NCA is added to the polyaminoacid chain and the amido containing metallacyle is regenerated for further polymerization. In a preferred embodiment of the invention, the efficiency of the initiator is controlled by allowing the reaction to proceed in a solvent selected for its ability to influence the reaction. In a specific embodiment of the invention, the solvent is selected from the group consisting of ethyl acetate, toluene, dioxane, acetonitrile, THF and DMF.

Another embodiment of the invention provides a method of making an amido-containing metallacycle comprising combining an amount of an α-aminoacid-N-carboxyanhydride monomer with an initiator molecule comprising a low valent transition metal-Lewis Base ligand complex so that an amido-containing metallacycle is formed.

Another embodiment of the invention provides compositions consisting of five or six membered amido-containing metallacycles comprising molecules of the general formulae:

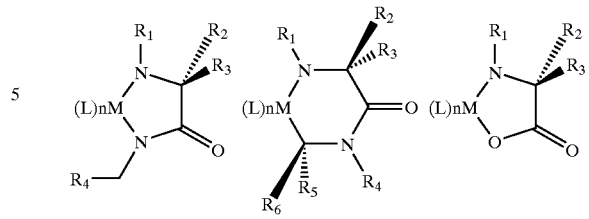

wherein
- M is a low valent transition metal;
- L is a Lewis Base ligand;
- each of R1, R2, R3, R5 and R6 (independently) is a moiety selected from the group consisting of the side chains of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine; and
- R4 is a hydrogen moiety or a polyaminoacid chain.

In preferred embodiments of these compositions, the metal is a transition metal selected from the group consisting of nickel, palladium, platinum, cobalt, rhodium, iridium and iron and the Lewis Base ligand is selected from the group consisting of pyridyl ligands, diimine ligands, bisoxazoline ligands, alkyl phosphine ligands, aryl phosphine ligands, tertiary amine ligands, isocyanide ligands and cyanide ligands.

In yet another embodiment, the invention provides block copolypeptide compositions having characteristics which have been previously unattainable through conventional techniques. A specific embodiment of this invention consists of a polypeptide composition comprising a block polypeptide having a number of overall monomer units that are greater than about 100 amino acid residues and a distribution of chain-lengths at least about 1.01<Mw/Mn<1.25. In a related embodiment, the polypeptide has a number of overall monomer units that are greater than about 250 amino acid residues. In a specific embodiment, the copolypeptide consists of a least 3 blocks of consecutive identical amino acid monomer units. In a specific embodiment of this invention, at least one of the blocks is components is γ-benzyl-L-glutamate.

As examples of preferred embodiments of the invention, a series of initiators for the polymerization of amino acid-N-carboxyanhydrides (NCAs) into block copolypeptides based on a variety of metals and ligands are described. These initiators are substantially different in nature from all known conventional initiators used to polymerize NCAs and are also unique in being able to control these polymerizations so that block copolymers of amino acids can be prepared. Specifically, these initiators eliminate chain transfer and chain termination side reactions from these polymerizations resulting in narrow molecular weight distributions, molecular weight control, and the ability to prepare copolymers of defined block sequence and composition. All of these traits have previously been unobtainable using conventional initiator systems. Furthermore, the initiators described herein are readily prepared in a single step from commercially available materials.

The discovery of this new class of initiators and methods for their use allows for the elimination of side reactions from NCA polymerizations and further allows the preparation of well-defined block copolypeptides. Formation of an illustrative example of our initiator results from the oxidative-addition reaction of an NCA monomer to a zerovalent nickel complex, bipyNi(COD); bipy=2,2'-bipyridyl, COD=1,5-cyclooctadiene. This reaction is similar to the known oxidative-addition of cyclic anhydrides to zerovalent nickel to yield acyl-carboxylato divalent nickel complexes (see equation 5 below).

(5)

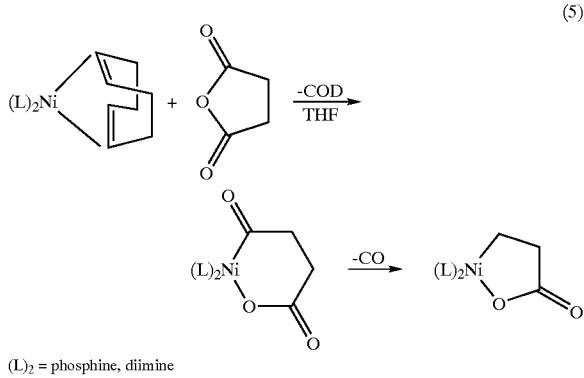

$(L)_2$ = phosphine, diimine

While this reaction is similar to these known oxidative-addition reactions, the reaction occurring in the formation of the molecules disclosed herein is without precedent.

The methods and initiator compositions disclosed herein allow the preparation of complex polypeptide biomaterials which have potential applications in biology, chemistry, physics, and materials engineering. Potential applications include medicine (drug delivery, tissue engineering), "smart" hydrogels (environmentally responsive organic materials), and in organic/inorganic biomimetic composites (artificial bone, high performance coatings).

DETAILED DESCRIPTION OF THE INVENTION

I. Definitions

Figure 1:
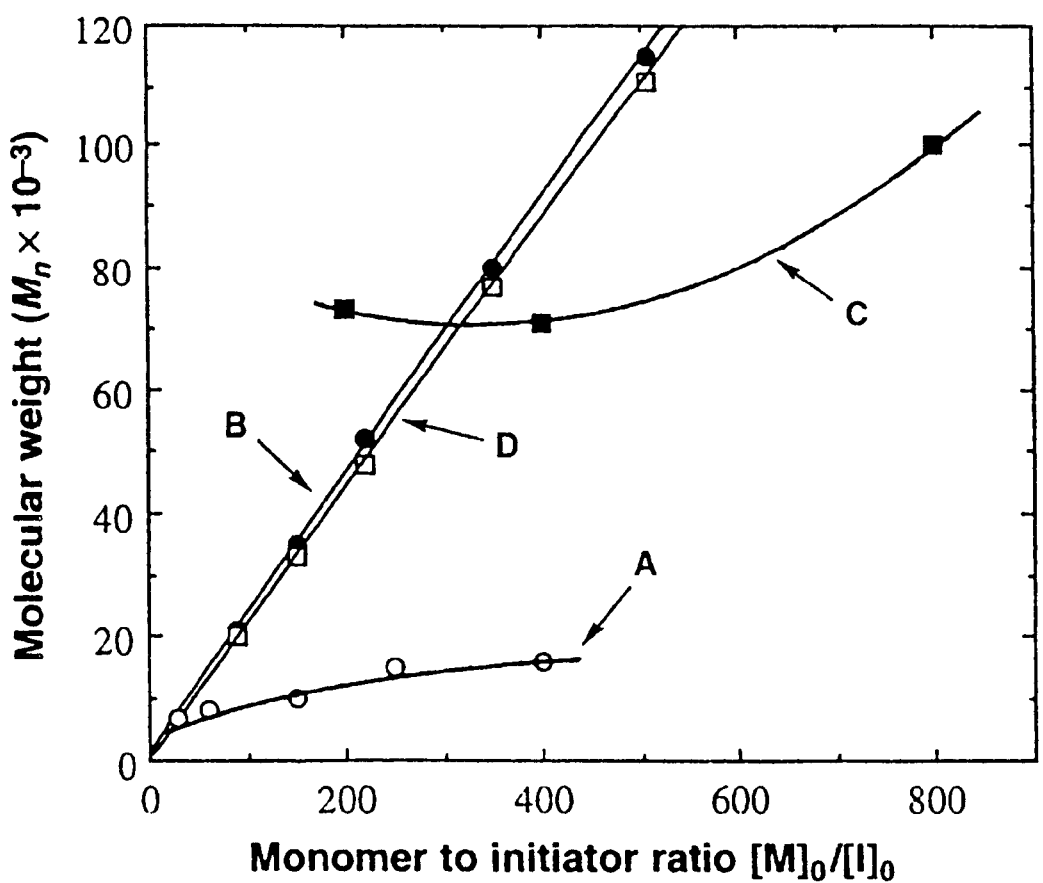
FIG. 1 compares the abilities of different initiators to control molecular weight of PBLG as a function of initiator concentration in polymerizations of Glu-NCA: A, phenethylamine initiator; B, bipyNi(COD) initiator; C, sodium tert-butoxide initiator; D, theoretical molecular weight calculated from $[M]_0/[I]_0$. All polymerizations were run in anhydrous DMF at 25° C. for 1 day in sealed tubes. Molecular weight ($M_n$) was determined by tandem GPC/light scattering in 0.1M LiBr in DMF at 60 °C.

The term "block copolypeptide" as used herein refers to polyaminoacids comprised of sequences containing domains ("blocks") of at least two continuous residues of a single type of amino acid covalently linked to at least two continuous residues of a distinct single type of amino acid by a conventional polyamide linkage found in polypeptides (see e.g. Example 1). The number, length, order, and composition of these sequences can vary to include all possible amino acids in any number of repeats. Preferably the total number of overall monomer units (residues) in the block copolypeptide is greater than 100 and the distribution of chain-lengths in the block copolymer is about 1.01<Mw/Mn<1.25, where Mw/Mn=weight average molecular weight divided by number average molecular weight.

The terms "protection" and "side-chain protecting group" as used herein refer to chemical substituents placed on reactive functional groups, typically nucleophiles or sources of protons, to render them unreactive as protic sources or nucleophiles. The choice and placement of these substituents was according to literature procedures. M. Bodanszky, et al., *The practice of Peptide Synthesis*, 2$^{nd}$ Ed., Springer, Berlin/Heidelberg, (1994).

II. Methods and Compositions of the Invention

The methods and compositions disclosed herein teach new ways to polymerize amino acids and to add amino acids to polyamino acid chains. Further, the initiators and amido-containing metallacyle compositions disclosed herein allow the synthesis of block copolypeptides by eliminating of side reactions in favor of the chain-growth process (i.e. living polymerization), thus allowing multiple monomer additions to polyaminoacid chains. While the specific methods and initiator and amido-containing metallacyle compositions disclosed represent preferred embodiments of this invention, as discussed below, other embodiments are also contemplated.

In the examples below, general features for the formation of active metal initiators are discussed as well a means to determine initiator efficiency (see e.g. Example 3). Moreover disclosed herein are parameters for generating effective initiators as well assays to assess the activity of different initiator complexes and their ability to function in the disclosed methods. Moreover, disclosed herein are a number of different initiator compositions which were evaluated for their ability to work in this system. In addition, the Examples illustrate the effects of different solvents on the various polypeptide addition reactions. Using these protocols, one skilled in the art may construct and then assess the ability of a new potential initiator molecule to function in the disclosed methods. Using the protocols disclosed herein, one may also assess the activity of different amido-containing metallacycles and their ability to function in the disclosed methods.

In providing new means to polymerize amino acids and to add amino acids to polyamino acid chains, the disclosed methods and compositions overcome a number of problems associated with complex polypeptide synthesis. Successful block copolypeptide synthesis requires elimination of side reactions in favor of the chain-growth process (i.e. living polymerization), thus allowing multiple monomer additions to each chain. L. J. Fetters, "Monodisperse Polymers" in *Encyclopedia of Polymer Science and Engineering 2nd Ed.*, Wiley-Interscience, New York, 10:19–25 (1987); O. Webster, "Living Polymerization Methods" *Science*, 251:887–893 (1991). This problem was addressed by utilizing the versatile chemistry of transition metals to mediate the addition of monomers to the active polymer chain-ends. T. J. Deming, "Polypeptide Materials: New Synthetic Methods and Applications" *Adv. Materials,* 9:299–311(1997). The wide range of selective chemical transformations and polymerizations that are catalyzed by transition metal complexes attests to the potential of this approach. J. P. Collman, et al., *Principles and Applications of Organotransition Metal Chemistry* 2nd Ed., University Science, Mill Valley, (1987). Attempts to use metal coordination complexes of conventional amine initiators to control the polymerizations have been described in the art. T. J. Deming, "Transition Metal-Amine Initiators for Preparation of Well-Defined Poly (γ-benzyl-L-glutamate)" *J. Am. Chem. Soc.,* 1997, 119:2759–2760 (1997). Use of metal-amine complexes for polymerization of γ-benzyl-L-glutamate N-carboxyanhydride, Glu-NCA as described herein, allowed the preparation of poly(γ-benzyl-L-glutamate), PBLG, with narrow molecular weight distribution ($M_w/M_n$=1.05–1.10) and some control over molecular weight. However, typical problems inherent in primary amine initiated polymerizations (i.e. slow propagation and chain transfer reactions) prevented use of these initiators for preparation of block copolypeptides.

The reaction chemistry of α-amino acid-N-carboxyanhydrides (NCAs) has been under study since these molecules are potential precursors to sequence specific peptides, polypeptides, and other amino acid containing compounds. H. R. Kricheldorf, *α-Aminoacid-N-Carboxyanhydrides and Related Materials,* Springer-Verlag, New York, (1987); H. R. Kricheldorf, in *Models of Biopolymers by Ring-Opening Polymerization,* Penczek, S. Ed., CRC Press, Boca Raton, (1990). NCAs are attractive peptide building blocks since they are readily prepared from amino acids and since they show no racemization at the chiral α-carbon either during preparation or in subsequent reactions. W. E. Hanby, et al., *Nature,* 161:132 (1948); A. Berger, et al., *J. Am. Chem Soc.,* 73:4084–4088 (1951). Utilization of NCAs, however, has been limited because of their complicated reactivity and tendency to uncontrollably polymerize. The living polymerization of NCAs and synthesis of block copolypeptides using nickel initiators has been reported. T. J. Deming, *Nature,* 390:386–389 (1997). This reference discloses stoichiometric reactions where NCAs oxidatively add regioselectively to sources of zerovalent nickel to yield complexes which subsequently rearrange to unprecedented amido-containing metallacycles. When complexed with donor ligands, the nickelacycles are efficient NCA polymerization initiators.

Figure 3:
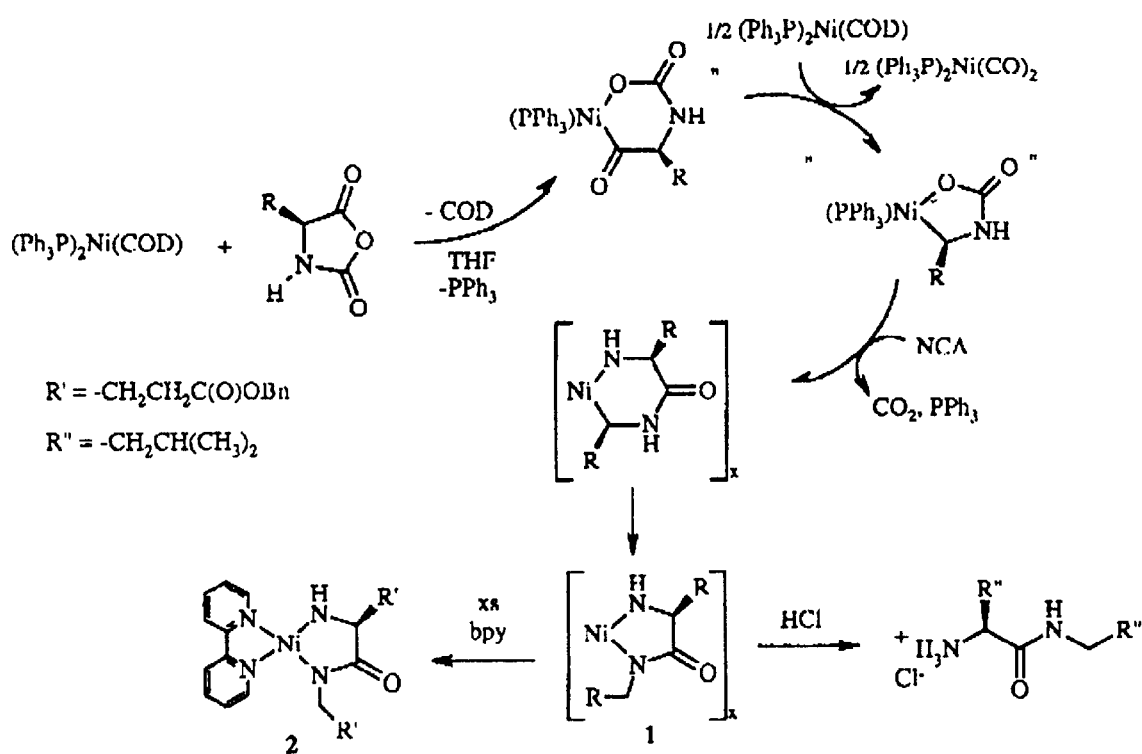
FIG. 3 shows 2 chemical reaction schemes associated with amino acid derived nickelacycles, intermediates in nickel initiator mediated polypeptide synthesis.

The oxidative addition of cyclic carboxylic acid anhydrides to nickel(0) was first reported by Uhlig and coworkers. E. Uhlig, et al., *Z. Anorg. Allg. Chem.,* 465:141–146 (1980). When succinic anhydride is added to $L_2Ni(COD)$ a six-membered acyl-carboxylato nickelacycle is initially formed which decarbonylates above ambient temperature to form a stable five-membered alkyl-carboxylato complex. $L_2$=donor ligand(s); COD=1,5-cyclooctadiene; bipy=2,2'-bipyridyl. With unsymmetric anhydrides, the regioselectivity of oxidative addition was found to vary with the donor ligand ($L_2$) and solvent. A. M. Castaño, et al., *Organometallics,* 13:2262–2268 (1994). When an NCA oxidatively adds to nickel(0) across the unsymmetric anhydride linkage, regioselectivity of addition is important in determining the nature and reactivity of the products. With both initial products, decarbonylation would be expected to be favored over decarboxylation due to the greater stability of the resulting five-membered metallacycles (see scheme 1 of FIG. 3). E. Uhlig, et al., *Z. Anorg. Allg. Chem.,* 465:141–146 (1980). The addition of NCAs to nickel(0) is of interest because the resulting metal-amido or metal-carbamato complexes might prove useful as reactive, chiral synthetic intermediates.

Unlike the initiators known in the art, the molecules described herein are a new class of initiators based on low valent metal-Lewis base complexes which are able to eliminate significant competing termination and transfer steps from NCA polymerizations and allow preparation of well-defined block copolypeptides. Formation of these initiators results from the unprecedented reaction of an NCA monomer with a low valent metal-Lewis base complex such as a zerovalent nickel complex bipyNi(COD); bipy=2,2'-bipyridyl, COD=1,5-cyclooctadiene. This reaction is similar to the oxidative-addition of cyclic anhydrides to zerovalent nickel which yields divalent nickel metallacycles (see equation 6 below). E. Uhlig, et al., "Reaktionen cyclischer Carbonsaeureanhydride mit (α,α'-Dipyridyl)-(cyclooctadien-1,5)-nickel" *Anorg. Allg. Chem.,* 465:141–146 (1980); K. Sano, et al., "Preparation of Ni- or Pt-Containing Cyclic Esters by Oxidative Addition of Cyclic Carboxylic Anhydrides and Their Properties" *Bull. Chem. Soc. Jpn.,* 57:2741–2747 (1984); A. M. Castaño, et al., "Reactivity of a Nickelacycle Derived from Aspartic Acid: Alkylations, Insertions, and Oxidations" *Organometallics,* 13:2262–2268 (1994).

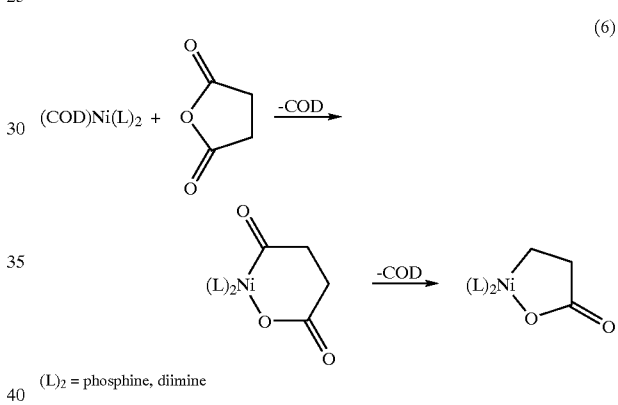

(6)

Activation and polymerization of NCAs through oxidative ring opening of the anhydride, however, is without precedent. Successful polymerization of L-proline NCA, which lacks a proton bound to nitrogen, using bipyNi(COD) supports the hypothesis of oxidative addition across the anhydride bond, rather than reaction at the N—H bond. In this context, it is observed that the initial oxidative addition to the NCA can occur at either side of the anhydride bond (for example, O—$C_5$ for nickel, cobalt and iron and both O—$C_5$ and O—$C_2$ for rhodium and iridium).

Since NCAs are unsymmetrical anhydrides, the oxidative-addition of NCAs can yield two distinct isomeric products (see equation 7 below).

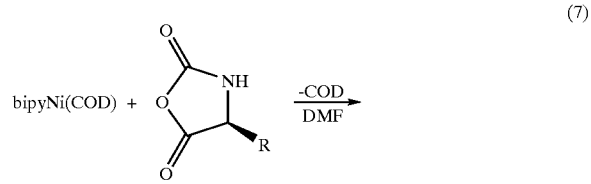

(7)

-continued

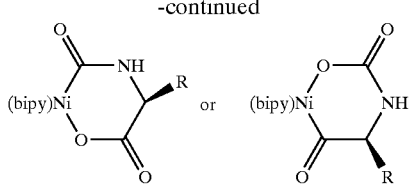

In practicing one embodiment of the invention, it is found that the addition of NCAs to nickel was completely regioselective for ring opening across the O—$C_5$ bond. Reaction of bipyNi(COD) with $^{13}C_2$-L-leucine NCA and $^{13}C_5$-L-leucine NCA yielded oxidative addition products and bipyNi$(CO)_2$ which were examined by $^{13}C$ NMR and FTIR spectroscopy. Detection of bipyNi$(^{12}CO)_2$ (FTIR(THF): n(CO)= 1978, 1904 $cm^{-1}$) from the reaction of $^{13}C_2$-L-leucine NCA, and bipyNi$(^{13}CO)_2$ (FTIR(THF): n(CO)=1934, 1862 $cm^{-1}$; $^{13}C$ NMR(DMF-$d_7$): d 198 (Ni—$\underline{C}$O)) from the reaction of $^{13}C_5$-L-leucine NCA identified the regiochemistry of the product (see equation 8 below). In dimethylformamide (DMF), a good solvent for polypeptides, this addition product was found to be completely active for polymerization of additional NCA monomers.

(8)

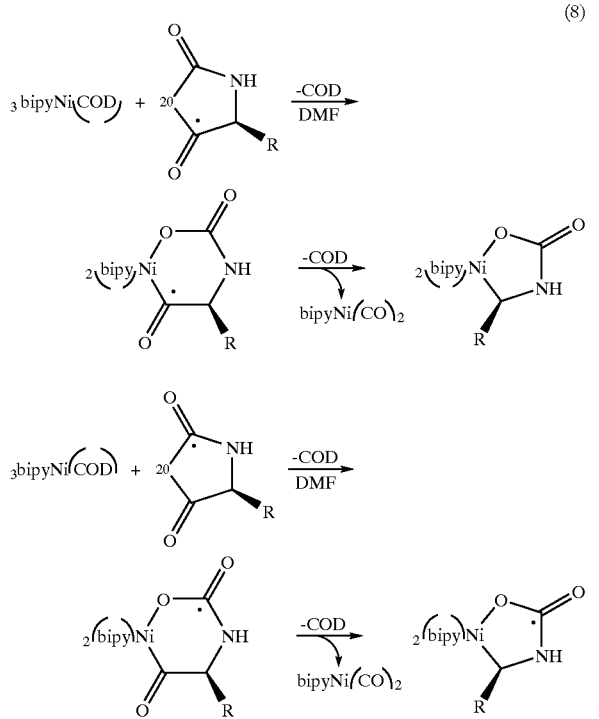

As illustrated in Example 3 below, the efficiency of various initiators can be analyzed through polymerization experiments with Glu-NCA. The resulting polymer, PBLG, is α-helical in many solvents, has been extensively studied, and is readily characterized. H. Block, *Poly(γ-benzyl-L-glutamate) and Other Glutamic Acid Containing Polymers*, Gordon and Breach, New York, (1983). Number-average molecular weight of PBLG samples formed using bipyNi(COD) in DMF was found to increase linearly as a function of the initial monomer to initiator ratios, indicating the absence of chain-breaking reactions. L. J. Fetters, "Monodisperse Polymers" in *Encyclopedia of Polymer Science and Engineering 2nd Ed.*, Wiley-Interscience, New York, 10:19–25 (1987); O. Webster, "Living Polymerization Methods" *Science*, 251:887–893 (1991). Such control over polypeptide molecular weight is a substantial improvement over conventional NCA polymerization systems (see FIG. 1). The polymers possessed narrow molecular weight distributions ($M_w/M_n$=1.05–1.15) and were obtained in excellent yields (95–99% isolated). Kinetic analysis also showed that the polymerizations were well behaved. The polymerizations were first order in monomer concentration over 4 half-lives in DMF ($k_{obs}$=2.7(1)×$10^{-4}$ $s^{-1}$ at 298K; [bipyNi(COD)]=0.67 mM) showing none of the complexities of traditional NCA polymerizations. Our initiating system displays all of the characteristics of a living chain growth process for Glu-NCA. Analysis of other NCA monomers (e.g. ε-carbobenzyloxy-L-lysine N-carboxyanhydride, Lys-NCA) also yielded controlled polymerizations, illustrating the general utility of our initiating system for preparation of well-defined block copolypeptides with a variety of architectures.

Illustrative embodiments of the invention that are disclosed in the examples below include diblock copolymers composed of amino acid components γ-benzyl-L-glutamate and ε-carbobenzyloxy-L-lysine. The polymers were prepared by addition of Lys-NCA to bipyNi(COD) in DMF to afford living poly(ε-carbobenzyloxy-L-lysine), PZLL, chains with organometallic end-groups capable of further chain growth. Glu-NCA was added to these polymers to yield the PBLG-PZLL block copolypeptides. The evolution of molecular weight through each stage of monomer addition was analyzed using gel permeation chromatography (GPC) and data are given in Table A in Example 2 below. Molecular weight was found to increase as expected upon growth of each block of copolymer while polydispersity remained low, indicative of successful copolymer formation. A. Noshay, et al., *Block Copolymers*, Academic Press, New York, (1977).

Figure 2:
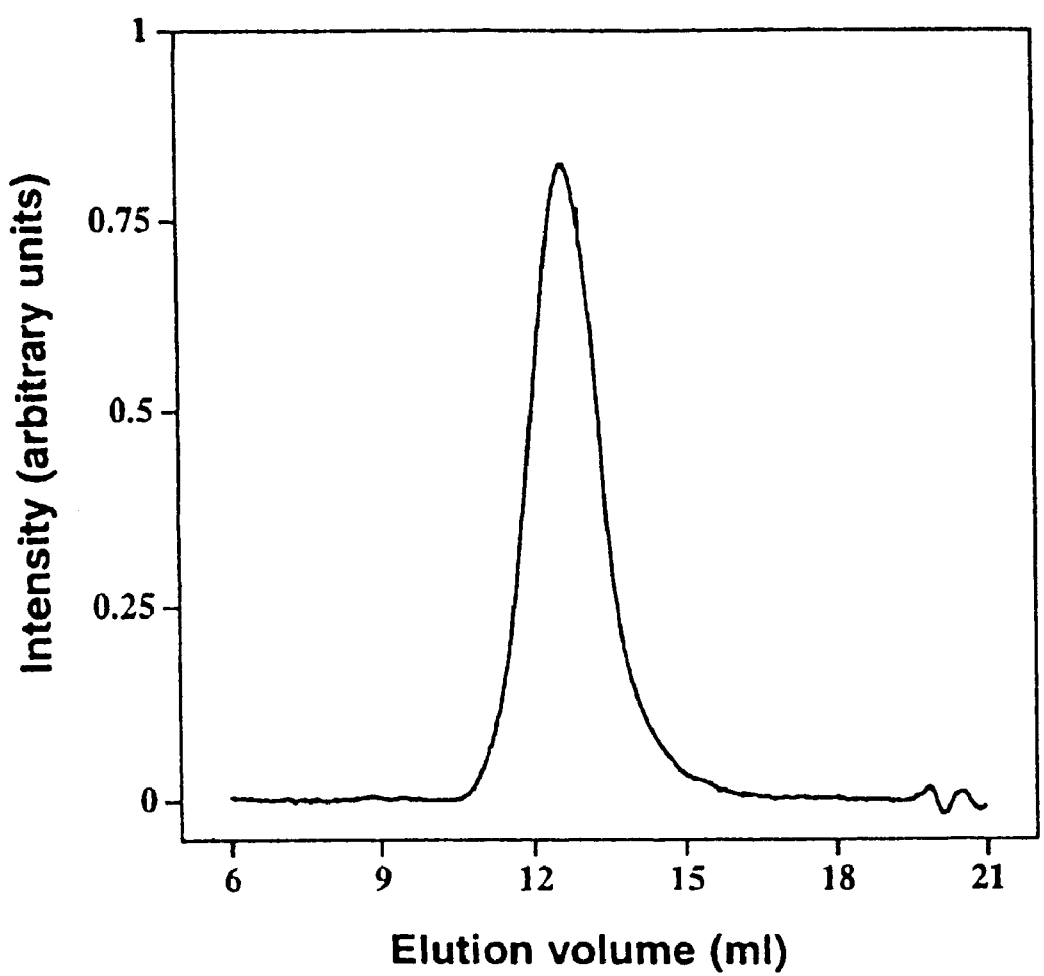
FIG. 2 is a chromatogram of a $PBLG_{0.78}$-b-$PZLL_{0.22}$ diblock copolymer prepared by sequential addition of Lys-NCA and Glu-NCA to bipyNi(COD) initiator in DMF. The polymer was injected directly into the GPC, eluted using 0.1M LiBr in DMF at 60° C. through $10^5$ Å and $10^3$ Å Phenomenex 5 μm columns, and detected with a Wyatt DAWN DSP light scattering detector and Wyatt Optilab DSP.

The chromatograms of the block copolypeptides showed single sharp peaks illustrating the narrow distribution of chain lengths (See FIG. 2). Copolypeptide compositions were easily adjusted by variation of monomer feed compositions, both being equivalent. Successful preparation of copolypeptides of reverse sequence (i.e. PZLL-PBLG) and of triblock structure (e.g. $PBLG_{0.39}$-b-$PZLL_{0.22}$-b-$PBLG_{0.39}$; $M_n$=256,000, $M_n/M_n$=1.15) illustrate the sequence control using the nickel initiator.

Block copolymerizations were not restricted to the highly soluble polypeptides PBLG and PZLL. Copolypeptides containing L-leucine and L-proline, both of which form homopolymers which are insoluble in most organic solvents (e.g. DMF) have also been prepared. Data for these copolymerizations are given in Table A in Example 2 below. Because of the solubilizing effect of the PBLG and PZLL blocks, all of the products were soluble in the reaction media indicating the absence of any homopolymer contaminants. The block copolymers containing L-leucine were found to be strongly associating in 0.1M LiBr in DMF, a good solvent for PBLG and PZLL. Once deprotected, the assembly properties of these materials are expected make them useful as tissue engineering scaffolds, drug carriers, and morphology-directing components in biomimetic composite formation.

Block copolymers have played an important part in materials science and technology because they allow the effective combination of disparate properties in a single material. Block copolymers of styrene and dienes, for example, are rubbers at room temperature (a characteristic of the polydiene phase) but can be moulded at temperatures above the glass transition of the polystyrene phase. This distinguishes the block copolymers from most conventional rubbers, which must be chemically cross-linked (vulcanized) in order to withstand the stresses that they encounter in use. Because chemical cross-linking is irreversible, it must be done while making the final part; and cross-linked rubber is difficult to reprocess. The 'cross-linking' step for styrene-diene block copolymers is instead a physical association of chains in the glassy polystyrene domains: the tendency of the two different chain sections to clump together, like with like. This association is robust enough to bear loads at room temperature, but is readily reversible upon heating.

Well-defined block copolymers assemble spontaneously into a variety of intriguing nanostructures, and other, aligned nano-structure arrays can be made using fluid flow or other fields. Z. R. Chen, et al., *Science,* 277:1248–1253 (1997). Because of this, block copolymers have enjoyed great commercial success, as well as the ardent attentions of polymer physicists. But block copolymers of amino acids have been little studied, largely because our synthetic methods do not have fine enough control to produce well-defined structures. F. Cardinauz, et al., *Biopolymers,* 16:2005–2028 (1977). The same is true of the synthesis of block copolypeptides for use as biomaterials or as selective membranes—the potential advantages of the protein-like architectures have remained unrealized for want of adequate synthetic tools. The disclosed methods and compositions promise to change that. By treating the monomer of interest with an initiator such as the zero-valent nickel complex bipyNi(COD), where bipy is 2,2'-bipyridyl and COD is 1,5-cyclooctadiene and adding NCAs yields an intermediate molecule that can be isolated and that remains active towards further ring-opening polymerization, and the target polypeptide can be prepared with essentially 100 percent yield.

The ideal living polymerization is characterized by fast initiation and an absence of the termination and chain transfer steps that in most polymerization systems compete with propagation of the growing chain. When these conditions are realized, all polymer chains begin growing at about the same time and continue to grow until the monomer has been exhausted. The average number of monomer residues per chain is then simply the molar ratio of monomer to initiator, and the distribution of chain lengths is described by Poisson statistics. M. Szwarc, *Carbanions, Living Polymers, and Electron-Transfer Processes*, Wiley, New York (1968). As disclosed herein, these conditions have been met in the polymerization of NCAs by bipyNi(COD). The distribution of chain lengths is narrow, consistent with Poission statistics, and the rate of polymerization is proportional to monomer concentration, indicating that the number of active chain ends remains constant throughout the reaction.

It is the absence of termination and transfer that makes living polymerization so powerful for synthesizing block copolymers. Because the growing chains remain active even after the monomer has been exhausted, adding a second monomer at that stage results in the growth of a second block distinct in composition from the first. Proper choice of monomers allows one to engineer the kinds of combinations of properties described above: rubbery glassy; hydrophilic and hydrophobic; conducting and insulating; and so on.

A variety of illustrative initiator complexes useful in the generation of block copolypeptides are described herein such as those generated using bis-1,5-cyclooctadiene nickel (Ni(COD)$_2$) as the nickel source and 2,2'-bipyridyl(bipy) as the donor ligand component in tetrahydrofuran (THF) solvent. As discussed below and as shown in Tables 4 and 5, the use of other sources of zerovalent nickel (e.g. nickel-olefin complexes, nickel-carbonyl complexes, nickel-isocyanide or cyanide complexes, and other specific ligands such as PR$_3$ [R=Me, Et, Bu, cyclohexyl, phenyl], R$_2$PCH$_2$CH$_2$PR$_2$ [R=Me, phenyl], α,α'-diimine ligands [1,10-phenanthroline, neocuproine], diamine ligands [tetramethylethylene diamine], and isocyanide ligands [tert-butyl isocyanide and related nickel nitrogen or phosphorous donor ligand complexes) can work in the complexes of the present invention to initiate these polymerizations.

As shown in Example 3 below, in addition to bis-1,5-cyclooctadiene nickel (Ni(COD)$_2$), other sources of zerovalent nickel (e.g. Ni(CO)$_4$) as well as other low valent metals in the initiator complexes have been used successfully in these methods. Illustrative metals useful in the generation of initiators are "low valent" transition metals, in particular the metals of Group 8 of the Periodic Table and illustrative examples of initiators using such metals is provided in Table 5. This group includes the metals, Fe, Ru, Os, Co, Rh, Ir, Ni, Pd and Pt. The "low valent" forms of the metals implies that the metals are in low oxidation states. For Ni, Pd, Pt, Co, and Fe this means the zerovalent (0) oxidation state. For Ir and Rh, this means the monovalent (+1) oxidation state. For Ru and Os, this means the divalent (+2) oxidation state. See the complexes in Table 5 for relevant examples. The term, "Low valent metal" also extends to other metals in an oxidation state such the metal may undergo a 2 electron oxidation.

As shown in Example 3 below, in addition to using 2,2'-bipyridyl(bipy) as the donor ligand component, a variety of other donor ligands can be used in the initiator complexes. As shown in Table 4, ligands which can be used to bind to the initiator metals complexes need to comprise a non nucleophilic electron donor comprising a Lewis base and can consists of a variety of groups which have this property including those that are pyridyl based (see e.g. entry 2-144, Table 4), diimine (see e.g. DIPRIM, 2-148), bisoxazoline (see e.g. DPOX, 3–2), alkyl phosphine (see e.g. dmpe, 2-148), aryl phosphine (see e.g. PPh3, 2-151), tertiary amine (see e.g. tmeda, 3-10), isocyanide or cyanide (see e.g. 3-34), or combinations of these ligands. Generally, the ligands are bidentate (coordinate through 2 atoms) or are composed of 2 equivalents of monodentate ligands. Tridentate ligands can also be used (e.g. terpyridine). The ligands generally are bound to the metal through N, P, or C atoms of the molecule. Other N or P donor ligands, similar to those mentioned above (i.e. neutral, non-nucleophilic, aprotic) can also support these initiators.

As illustrated in the references cited above, NCA monomers are well known in the art (see e.g. H. R. Kricheldorf, *α-Aminoacid-N-Carboxyanhydrides and Related Materials,* Springer-Verlag, New York, (1987)). Moreover, the use of a variety of NCA monomers in methods of polypeptide synthesis is well known in the art. For example the stepwise synthesis of polypeptides using NCAs (or derivatives thereof) is disclosed in U.S. Pat. No. 3,846,399 (incorporated by reference herein). In addition, U.S. Pat. No. 4,267,344 discloses N-substituted N-carboanhydrides of a amino acids and their application in the preparation of peptides (incorporated by reference herein).

By providing examples of NCAs polymerized by zerovalent nickel catalysts under 'living' polymerization conditions; that is, conditions free of termination and chain transfer, the disclosed methods and compositions allow for the generation and manipulation of peptides in manners that have not previously been possible. Living polymerizations allow the synthesis of polymers of predetermined molecular weights and narrow molecular-weight distribution; and, perhaps more importantly, the preparation of well-defined block copolymers in which long sequences of each of the individual monomer residues are linked together at a single site. The advantages of living polymerizations, which once were reserved for a small subset of polymerizable monomers, can now be extended to NCAs and to the preparation of high-molecular-weight polypeptides and block copolypeptides with unusual and useful properties.

As discussed above, embodiments of the present invention provide a number of novel methods and compositions for the generation of polypeptides having varied material properties. The description and illustrative examples disclosed herein provide a number of exemplary embodiments of the invention. Specific embodiments of the invention include methods of adding aminoacid-N-carboxyanhydrides (NCAs) to polyaminoacid chains by exposing the NCA to solutions containing polyaminoacid chains having an amido amidate metallacyle end groups and reacting the NCA with the amido amidate metallacyle end group so that the NCA is added to the polyaminoacid chain. Addition embodiments include methods of controlling the polymerization of aminoacid-N-carboxyanhydrides by reacting NCAs with initiator molecules and allowing initiator complexes to regioselectively open the ring of the NCAs through oxidative addition across the O—$C_5$ or O—$C_2$ anhydride bond resulting a controlled polypeptide polymerization. Other embodiments include methods for making amido-containing metallacycles are disclosed herein. Additional embodiments of the invention include compositions for use in peptide synthesis and design including five and six membered amido-containing metallacycles and block copolypeptides.

One embodiment of the invention provides a method of making a block copolypeptide consisting of combining an amount of a first aminoacid-N-carboxyanhydride monomer with an initiator molecule comprising a low valent transition metal-Lewis Base ligand complex so that a polyaminoacid chain is generated and then combining an amount of a second aminoacid-N-carboxyanhydride monomer with the polyaminoacid chain so that the second aminoacid-N-carboxyanhydride monomer is added to the polyaminoacid chain. In a preferred embodiment of this method, the initiator molecule combines with the first aminoacid-N-carboxyanhydride monomer to form an amido containing metallacycle intermediate of the general formulae:

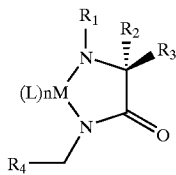

wherein
M is the low valent transition metal;
L is the Lewis Base ligand;
and each of R1 and R2 and R3 independently consist of a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and
R4 is the polyaminoacid chain.

In a highly preferred embodiment of this method, making a block copolypeptide, the low valent transition metal is selected from the group consisting of nickel, palladium, platinum, cobalt, rhodium, iridium and iron. In another preferred embodiment of this method, the Lewis Base ligand is selected from the group consisting of pyridyl ligands, diimine ligands, bisoxazoline ligands, alkyl phosphine ligands, aryl phosphine ligands, tertiary amine ligands, isocyanide ligands and cyanide ligands. In yet another preferred embodiment of this method, the first α-aminoacid-N-carboxyanhydride monomer is an NCA is an α-aminoacid-N-carboxyanhydride selected from the group consisting of side-chain protected NCA formed from arginine, asparagine, aspartic acid, cysteine, glutamic acid, glutamine, histidine, lysine, methionine, serine, threonine, tryptophan, and tyrosine or an amino acid side chain selected from the group consisting of side-chain NCA formed from alanine, glycine, isoleucine, leucine, phenylalanine, proline and valine.

A related embodiment of the invention consists of a method of adding an aminoacid-N-carboxyanhydride (NCA) to a polyaminoacid chain having an amido containing metallacycle end group comprising combining the NCA with the polyaminoacid chain so that the NCA is added to the polyaminoacid chain. In a preferred embodiment of this method, the amido containing metallacycle end group is of a formulae selected from the group consisting of:

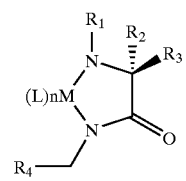

wherein
M is the low valent transition metal;
L is the Lewis Base ligand;
R1 comprises a constituent found in a side chain of an amino acid (e.g. a hydrogen for glycine or a methyl group for alanine etc.) selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;
R2 comprises a constituent found in a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;
R3 comprises a constituent found in a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and
R4 is the polyaminoacid chain.

In a preferred embodiment of the method of adding an aminoacid-N-carboxyanhydride (NCA) to a polyaminoacid chain having an amido containing metallacycle end group, the metal group of the amido containing metallacycle is a transition metal selected from the group consisting of nickel, palladium, platinum, cobalt, rhodium, iridium and iron and the Lewis Base ligand is selected from the group consisting of pyridyl ligands, diimine ligands, bisoxazoline ligands, alkyl phosphine ligands, aryl phosphine ligands, tertiary amine ligands, isocyanide ligands, and cyanide ligands. In specific embodiments of the invention, the NCA is an α-aminoacid-N-carboxyanhydride selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Another embodiment of the invention disclosed herein entails a method of polymerizing aminoacid-N-carboxyanhydride monomers by combining a NCA monomer with an initiator molecule complex comprised of a low valent transition metal-Lewis Base ligand. A specific embodiment of the invention disclosed herein entails a method of polymerizing aminoacid-N-carboxyanhydride monomers having a ring with a O—$C_5$ and a O—$C_2$ anhydride bond which consists of combining a first NCA monomer with an initiator molecule complex comprised of a low valent metal capable of undergoing an oxidative addition reaction wherein the oxidative addition reaction formally increases the oxidation state by two electrons; and an electron donor comprising a Lewis base, and then allowing the initiator molecule to open the ring of the first NCA through oxidative addition across either the O—$C_5$ or O—$C_2$ anhydride bond and then combine with a second NCA monomer, to form an amido-containing metallacycle and then allowing a third NCA monomer to combine with the amido containing metallacyle so that the amido nitrogen of the amido containing metallacyle attacks the carbonyl carbon of the NCA and the NCA is added to the polyaminoacid chain the amido containing metallacyle is regenerated for further polymerization. In a preferred embodiment of the invention, the efficiency of the initiator is controlled by allowing the reaction to proceed in a solvent selected for its ability to influence the reaction. In a specific embodiment of the invention, the solvent is selected from the group consisting of ethyl acetate, toluene, dioxane, acetonitrile, THF and DMF.

Another embodiment of the invention provides a method of making an amido-containing metallacycle comprising combining an amount of an α-aminoacid-N-carboxyanhydride monomer with an initiator molecule comprising a low valent transition metal-Lewis Base ligand complex so that an amido-containing metallacycle is formed.

Another embodiment of the invention entails a five or six membered amido-containing metallacycle comprising molecules of the general formula:

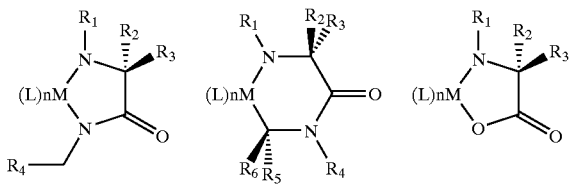

wherein "M" is a low valent transition metal capable of undergoing an oxidative addition reaction, "L" is an electron donor such as a Lewis base and "R#" comprises any organic substituent not bearing free amine, hydroxyl, carboxylic acid, sulfhydryl, isocyanate, imidazole, or other highly protic or nucleophilic functionality. These functionalities may be present, however, if suitably chemically protected to render them unreactive as protic sources or nucleophiles. Effective R substituents on the above structures exhibit a number of properties. For example, as disclosed in the examples below, the R substituents on the above structures are typically encompassed by the structures of the side chain substituents of amino acids or derivatives thereof. In particular, in most cases, R1 (and R4 in the center structure) is a proton. Independently, each of R2 and R3 (and R5 and R6) are typically selected from the side chain substituents of amino acids. Typically, one of the substituents (such as R1) is a proton (H), while the others can be different side chain group of a specific amino acid. The placement of the proton (as either R2 or R3) is determined by the amino acid being of the L or D configuration. The side chain will be one of those from the family of naturally occurring L- or D-amino acids, or synthetic amino acids or derivatives thereof. Naturally occurring L- or D-amino acids (e.g. alanine, arginine, asparagine, aspartic acid, γ-carboxyglutamate, cysteine, glutamic acid, glutamine, glycine, histidine, hydroxyproline, isoleucine, leucine, lysine, methionine, phenylalanine, proline, serine, threonine, tryptophan, tyrosine and valine) and synthetic amino acids or derivatives thereof are well known in the art. The side-chains of amino acids bearing polar functional groups (e.g. $NH_2$, COOH, SH, imidazole) can be blocked with standard peptide protecting groups.

In a preferred embodiment, the metal is a group 8 transition metal and the donor ligand(s) can be any of those given in Table 4. In a another preferred embodiment, the metal is nickel and the donor ligand is a 2,2'-bipyridyl(bipy) moiety. In another preferred embodiment, the R2 or R3 group comprises an amino acid side chain selected from the group consisting of side-chain protected NCA formed from arginine, asparagine, aspartic acid, cysteine, glutamic acid, glutamine, histidine, lysine, methionine, serine, threonine, tryptophan, and tyrosine or an amino acid side chain selected from the group consisting of side-chain NCA formed from alanine, glycine, isoleucine, leucine, phenylalanine, proline and valine.

Another embodiment of the invention entails a block copolypeptide wherein the number of overall monomer units (residues) in the block copolypeptide is greater than about 100; and the distribution of chain-lengths in the block copolymer composition is at least about $1.01<Mw/Mn<1.25$, where Mw/Mn=weight average molecular weight divided by number average molecular weight. In one embodiment, the block copolypeptide has 10 consecutive identical amino acids per block. In a preferred embodiment, the block copolypeptide is composed of amino acid components γ-benzyl-L-glutamate- and ε-carbobenzyloxy-L-lysine. In another preferred embodiment, the copolypeptide is a poly (ε-benzyloxycarbonyl-L-Lysine-block-γ-benzyl-L-glutamate), PZLL-b-PBLG, diblock copolymer. In yet another preferred embodiment the copolypeptide is a poly (γ-benzyl-L-glutamate-block-ε-benzyloxycarbonyl-L-Lysine-block-γ-benzyl-L-glutamate) triblock copolymer. In related embodiments, the number of consecutive monomer units (residues) in the block copolypeptide is greater than about 50 or 100 or 500 or 1000 (see e.g. the examples disclosed in Tables A and 3 below). In another related embodiment, the total number of overall monomer units (residues) in the block copolypeptide is greater than about 200, or greater than about 500, or greater than about 1000 (see e.g. the examples disclosed in Tables A and 3 below).

In addition to block copolypeptides, a variety of other related of polypeptides can be generated utilizing the methods disclosed herein wherein an initiator molecule combines with a first aminoacid-N-carboxyanhydride monomer to form an amido containing metallacycle intermediate of the five and six ring formulae disclosed herein. For example polypeptides can be generated where the domains can either be repeats (2 or greater) of identical amino acids, or can be repeats (2 or greater) of mixtures of distinct amino acids, or a combination of the two. The number, length, order, and composition of these domains can vary to include all possible amino acids in any number of repeats. Preferably the total number of overall monomer units (residues) in these polypeptides having segregated domains of mixed monomers is greater than 100 and the distribution of chain-lengths in the polypeptide is about 1.01<Mw/Mn<1.25, where Mw/Mn=weight average molecular weight divided by number average molecular weight.

An illustrative example of such a polypeptide could contain a sequence of, for example, 50 residues of leucine in one domain, followed by a statistical mixture of 20 valines and 20 glycines as the second domain, followed finally by a third domain of 40 phenylalanines. Such polypeptides are substantially different than "statistically random" copolymers where the entire polypeptide is composed of statistical mixtures of amino acids in the chains, and there are no strict block domains. One difference is that these polypeptides have segregated domains where one statistical mixture will be separated from the others. For example in a statistical copolymer, the amino acids will be distributed statistically (basically at random) along the entire polypeptide chain. In contrast, using the methods disclosed herein a polypeptide chain can be constructed such that in one domain there will be a statistical mixture of leucine and glycine, followed by a second domain consisting of a statistical mixture of glycine and valine. Although both copolymers have statistical mixtures of residues along the chain, these polypeptide differ in that the valine and leucine residues are segregated into separate domains.

The living polymerization methods for NCAs that are disclosed herein will lead to various polypeptides and block copolypeptides having a variety of new and useful properties. In this context, the disclosure provided herein demonstrates the successful synthesis of such materials, and creates a new family of polypeptides that link combination of acidic, basic and hydrophobic domains, all with excellent control of molecular architecture. The prospects for application in biomedical engineering, drug delivery and selective separations are excellent. In particular these features allow the preparation of complex polypeptide biomaterials which have potential applications in biology, chemistry, physics, and materials engineering. Potential applications include medicine (drug delivery, tissue engineering), "smart" hydrogels (environmentally responsive organic materials), and in organic/inorganic biomimetic composites (artificial bone, high performance coatings).

EXAMPLES

The following examples are offered by way of illustration and not by way of limitation. The disclosures of all citations in the specification are expressly incorporated herein by reference into this application in order to more fully describe the state of the art to which this invention pertains.

Example 1

Methods Using Amino Acid Derived Metallacycles: Intermediates in Metal Mediated Polypeptide Synthesis General Experimental Protocols and Reagents Infrared spectra were recorded on a Perkin Elmer 1605 FTIR Spectrophotometer calibrated using polystyrene film. Tandem gel permeation chromatography/light scattering (GPCILS) was performed on a Spectra Physics Isochrom liquid chromatograph pump equipped with a Wyatt DAWN DSP light scattering detector and Wyatt Optilab DSP. Separations were effected by $10^5$ Å and $10^3$ Å Phenomenex $5\mu$ columns using 0.1M LiBr in DMF eluent at 60° C. Optical rotations were measured on a Perkin Elmer Model 141 Polarimeter using a 1 mL volume cell (1 dm length). NMR spectra and bulk magnetic susceptibility measurements (Evans method) were measured on a Bruker AMX 500 MHz spectrometer. D. F. Evans, *J. Chem. Soc.*, 2003–2009 (1959); J. K. Becconsal, *J. Mol. Phys.*, 15:129–135 (1968). C, H, N elemental analyses were performed by the Microanalytical Laboratory of the University of California, Berkeley Chemistry Department. Chemicals were obtained from commercial suppliers and used without purification unless otherwise stated. $(COD)_2Ni$ was obtained from Strem Chemical Co., and $^{13}C_1$-L-leucine and $^{13}C$-phosgene were obtained from Cambridge Isotope Labs. L-leucine isoamylamide hydrochloride, γ-benzyl-L-glutamate NCA and L-leucine NCA were prepared according to literature procedures. M. Bodanszky, et al., *The practice of Peptide Synthesis*, $2^{nd}$ Ed., Springer, Berlin/Heidelberg, (1994); E. R. Blout, et al., *J. Am. Chem Soc.*, 78:941–950 (1956); H. Kanazawa, et al., *Bull. Chem Soc. Jpn.*, 51:2205–2208 (1978). Hexanes, THF, and THF-$d_8$ were purified by distillation from sodium benzophenone ketyl. DMF and DMF-$d_7$ were purified by drying over 4 Å molecular sieves followed by vacuum distillation.

(S)-[NiNHC(H)RC(O)NCH$_2$R]$_x$, R=—CH$_2$CH$_2$C(O)OCH$_2$C$_6$H$_5$; 1

In the dry box, Glu NCA (15 mg, 0.058 mmol) was dissolved in THF (0.5 mL) and added to a stirred homogeneous mixture of PPh$_3$ (31 mg, 0.12 mmol) and (COD)$_2$Ni (16 mg, 0.058 mmol) in THF (1.5 mL). The red/brown solution was stirred for 24 hours, after which the solvent was removed in vacuo to leave a dark red oily solid. This was extracted with hexanes (3×5 mL) to yield a red/brown hexanes solution and a yellow solid. Evaporation of the hexanes solution gave a red oil containing (PPh$_3$)$_2$Ni(CO)$_2$ [IR (THF): 2000, 1939 cm$^{-1}$ (νCO, vs); 18 mg; Literature: IR (CH$_2$ClCH$_2$Cl): 1994, 1933 cm$^{-1}$)], and drying of the solid gave the product as a yellow powder (10 mg, 75% yield). J. Chatt, et al., *J. Chem. Soc.*, 1378–1389 (1960). An $^1$H NMR spectrum could not be obtained in THF-$d_8$, most likely because of paramagnetism of the complex (only broad lines for the benzyl ester groups were observed). $\mu_{eff}$(THF, 293 K)=1.08 $\mu_B$. Osmotic molecular weight in THF (vs. ferrocene; ca. 7 mg/mL): 910 g/mol; this corresponds to a degree of aggregation of 1.94. IR (THF): 3281 cm$^{-1}$ (νNH, s br), 1734 cm$^{-1}$ (νCO, ester, vs), 1577 cm$^{-1}$ (νCO, amidate, vs). Anal. calcd. for NiC$_{23}$H$_{26}$N$_2$O$_5$: 58.87%C, 5.59%H, 5.96%N; found: 59.07%C, 5.67%H, 5.56%N. [α]$_D^{20}$ (THF, c=0.0034)=−71.

(S)-Cl$^-$·$^+$H$_3$NC(H)RC(O)NHCH$_2$R, R=—CH$_2$CH(CH$_3$)$_2$

In the dry box, L-leucine NCA (9.2 mg, 0.058 mmol) was dissolved in THF (0.5 mL) and added to a stirred homogeneous mixture of PPh$_3$ (31 mg, 0.12 mmol) and (COD)$_2$Ni (16 mg, 0.058 mmol) in THF (1.5 mL). The red/brown solution was stirred for 24 hours, after which the solvent was removed in vacuo to leave a dark red oily solid. This was extracted with cold hexanes (0° C., 3×2 mL) to yield a red/brown hexanes solution and a pale orange solid. Evaporation of the hexanes solution gave a red oil containing (PPh$_3$)$_2$Ni(CO)$_2$ [IR (THF): 2000, 1939 cm$^{-1}$ (νCO, vs); 17 mg], and drying of the solid gave an orange powder which could be purified by precipitation from THF/hexanes to give (S)-[NiNHC(H)RC(O)NCH$_2$R]$_x$, R=—CH$_2$CH(CH$_3$)$_2$ as a yellow powder (6 mg, 80% yield). An $^1$H NMR spectrum could not be obtained in THF-$d_8$, most likely because of paramagnetism of the complex. IR (THF): 3290 cm$^{-1}$ (vNH, s br), 1580 cm$^{-1}$ (nCO, amidate, vs). $[\alpha]_D^{20}$ (THF, c=0.001)=−185.

This product was dissolved in THF (5 mL) in a round bottom Schlenk flask in the dry box. The flask was placed under N$_2$ atmosphere on a Schlenk line and HCl (90 mL of a 1.0M solution in Et$_2$O) was then added. The yellow solution turned orange and then became hazy as it slowly turned green. After 2 h, the solvent was removed in vacuo to leave a green gummy solid. This solid was extracted with D$_2$O to isolate the amino acid containing products. The single isolated compound (4 mg, 73%) was found to be identical to an authentic sample of L-leucine isoamylamide hydrochloride (FIG. 1). $^1$H NMR (D$_2$O): δ3.94 (t, NH$_3$C<u>H</u>(CH$_2$CH(CH$_3$)$_2$)C(O)—, 1H, J=7.5 Hz), 3.33, 3.14 (dm, —C(O)NHC<u>H$_2$</u>CH$_2$CH(CH$_3$)$_2$, 2H, J$_{gem}$=107 Hz, J$_{mult}$=6 Hz, 13 Hz), 1.72 (dd, NH$_3$CH(C<u>H$_2$</u>CH(CH$_3$)$_2$)C(O)—, 2H, J=6 Hz, 7 Hz), 1.68 (m, NH$_3$CH(CH$_2$C<u>H</u>(CH$_3$)$_2$)C(O)—, 1H, J=7 Hz), 1.63 (m, —C(O)NHCH$_2$CH$_2$C<u>H</u>(CH$_3$)$_2$, 1H, J=7 Hz), 1.43 (ddd, —C(O)NHCH$_2$C<u>H$_2$</u>CH(CH$_3$)$_2$, 2H, J=7 Hz), 0.98, 0.96 (dd, NH$_3$CH(CH$_2$CH(C<u>H$_3$</u>)$_2$)C(O)—, 6H, J=6 Hz), 0.92, 0.90 (dd, —C(O)NHCH$_2$CH$_2$CH(C<u>H$_3$</u>)$_2$, 6H, J=6 Hz). $[\alpha]_D^{20}$ (THF, c=0.0033)=+10.3. Authentic Sample: $[\alpha]_D^{20}$ (THF, c=0.0033)=+10.5.

Reaction of (PPh$_3$)$_2$Ni(COD) with $^{13}$C$_2$-L-Leucine NCA

The procedure given above for the reaction using unlabeled L-leucine NCA was followed exactly, except for the substitution of $^{13}$C$_2$-L-Leucine NCA [prepared from L-leucine and O$^{13}$CCl$_2$; IR (CHCl$_3$): 3299 cm$^{-1}$ (vNH, s br), 1836, 1745 cm$^{-1}$ (vCO, anhydride, vs); $^{13}$C {$^1$H} NMR (THF-d$_8$): d 152 (s, —N<u>C</u>(O)O—]. The product was extracted with cold hexanes (0° C., 3×2 mL) to yield a red/brown hexanes solution and a pale orange solid. Evaporation of the hexanes solution gave a red oil containing (PPh$_3$)$_2$Ni(CO)$_2$ [IR (THF): 2000, 1939 cm$^{-1}$ (vCO, vs)], and drying of the solid gave an orange powder which could be purified by precipitation from THF/hexanes to give (S)-[NiNHC(H)RC(O)NCH$_2$R]$_x$, R=—CH$_2$CH(CH$_3$)$_2$ (5 mg, 66% yield). IR (THF): 3288 cm$^{-1}$ (vNH, s br), 1580 cm$^{-1}$ (vCO, amidate, vs).

Reaction of (PPh$_3$)$_2$Ni(COD) with $^{13}$C$_1$-L-Leucine NCA

The procedure given above for the reaction using unlabeled L-leucine NCA was followed exactly, except for the substitution of $^{13}$C$_5$-L-Leucine NCA [prepared from $^{13}$C$_1$-L-leucine and OCCl$_2$; IR (KBr): 3308 cm$^{-1}$ (vNH, s br), 1818, 1763 cm$^{-1}$ (vCO, anhydride, vs); $^{13}$C {$^1$H} NMR (THF-d$_8$): δ171 (s, —CHR<u>C</u>(O)O—]. The product was extracted with cold hexanes (0° C., 3×2 mL) to yield a red/brown hexanes solution and a pale orange solid. Evaporation of the hexanes solution gave a red oil containing (PPh$_3$)$_2$Ni($^{13}$CO)$_2$ [$^{13}$C{$^1$H}NMR (THF-d$_8$): δ202 (t, Ni($^{13}$<u>C</u>O)$_2$, J$_{P-C}$=15 Hz); IR (THF): 1954 1895 cm$^{-1}$ (n$^{13}$CO, vs)], and drying of the solid gave an orange powder which could be purified by precipitation from THF/hexanes to give (S)-[NiNHC(H)R$^{13}$C(O)NCH$_2$R]$_x$, R=—CH$_2$CH(CH$_3$)$_2$ (6 mg, 80% yield). IR (THF): 3290 cm$^{-1}$ (vNH, s br), 1536 cm$^{-1}$ (v$^{13}$CO, amidate, vs). $^{13}$C {$^1$H} NMR (THF-d$_8$): δ182 (s, [NiNHC(H)R$^{13}$<u>C</u>(O)NCH$_2$R]$_x$).

(S)-(2,2'-bipyridyl)NiNHC(H)RC(O)NCH$_2$R, R=—CH$_2$CH$_2$C(O)OCH$_2$C$_6$H$_5$; 2

In the dry box, a yellow solution of (S)-[NiNHC(H)RC(O)NCH$_2$R]$_x$, R=—CH$_2$CH$_2$C(O)OCH$_2$C$_6$H$_5$ (40 mg, 0.085 mmol) in DMF (0.5 mL) was added to a solution of 2,2'-bipyridyl (54 mg, 0.35 mmol) in DMF (0.5 mL). The homogeneous mixture was stirred for 2 d at 50° C., during which the color changed from yellow to blood red. THF (1 mL) and toluene (5 mL) were layered onto this solution resulting in precipitation of a red powder. This powder was reprecipitated from DMF/THF/toluene (1:2:10) two additional times to give (S)-(2,2'-bipyridyl)NiNHC(H)RC(O)NCH$_2$R, R=—CH$_2$CH$_2$C(O)OCH$_2$C$_6$H$_5$ as a red powder (49 mg, 92% yield). An $^1$H NMR spectrum could not be obtained in THF-d$_8$, most likely because of paramagnetism of the complex (only broad lines for the benzyl ester groups were observed). IR (THF): 3281 cm$^{-1}$ (vNH, s br), 1732 cm$^{-1}$ (vCO, ester, vs), 1597 cm$^{-1}$ (vCO, amidate, vs). Anal. calcd. for NiC$_{33}$H$_{34}$N$_4$O$_5$: 63.37%C, 5.49%H, 8.95%N; found: 63.72%C, 5.49%H, 8.86%N. $[\alpha]_D^{20}$ (THF, c=0.001)=−135.

Polymerization of Glu-NCA using (S)-(2,2'-bipyridyl)NiNHC(H)RC(O)NCH$_2$R, R=—CH$_2$CH$_2$C(O)OCH$_2$C$_6$H$_5$ In the dry box, Glu NCA (50 mg, 0.2 mmol) was dissolved in DMF (0.5 mL) and placed in a 25 mL reaction tube which could be sealed with a Teflon stopcock. An aliquot of (S)-(2,2'-bipyridyl)NiNHC(H)RC(O)NCH$_2$R, R=—CH$_2$CH$_2$C(O)OCH$_2$C$_6$H$_5$ (50 μl of a 40 mM solution in DMF) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (39 mg, 93% yield). $^{13}$C {$^1$H} NMR, $^1$H NMR, and FTIR spectra of this material were identical to data found for authentic samples of PBLG. H. Block, *Poly(g-benzyl-L-glutamate) and Other Glutamic Acid Containing Polymers*, Gordon and Breach, New York, (1983). GPC of the polymer in 0.1M LiBr in DMF at 60° C.: M$_n$=21,600; M$_w$/M$_n$=1.09. .

Reaction of (2,2'-bipyridyl)Ni(COD) with $^{13}$C$_2$-L-Leucine NCA

In the dry box, five equivalents of $^{13}$C$_2$-L-Leucine NCA (14.5 mg, 0.091 mmol) was added to a solution of bipyNi (COD) (5.9 mg, 0.018 mmol) in THF (1 mL). The mixture slowly turned from purple to red and was stirred for 16 hours. The crude product was isolated by evaporation of the solvent to yield a red oily solid. FTIR analysis of the crude reaction mixture confirmed the presence of (2,2'-bipyridyl) Ni(CO)$_2$ [IR (THF): 1978, 1904 cm$^{-1}$ (vCO, vs); Literature: IR (diethyl ether): 1983, 1914 cm$^{-1}$)], polyleucine [IR (THF): 1653 cm$^{-1}$ (vAmide I, vs); 1546 cm$^{-1}$ (vAmide II, vs)] as well as the $^{12}$C-amidate endgroup [IR(THF): ν(CO)= 1577 cm$^{-1}$]. R. S. Nyholm, et al., *J. Chem Soc.*, 2670 (1953). The reaction was also run in DMF-d$_7$ (0.5 mL) under otherwise identical conditions. $^{13}$C {$^1$H} NMR (DMF-d$_7$): δ126 (s, $^{13}$<u>C</u>O$_2$).

Reaction of (2,2'-bipyridyl)Ni(COD) with $^{13}$C$_5$-L-Leucine NCA

In the dry box, five equivalents of $^{13}$C$_5$-L-Leucine NCA (14.5 mg, 0.091 mmol) was added to a solution of bipyNi (COD) (5.9 mg, 0.018 mmol) in THF (1 mL). The mixture slowly turned from purple to red and was stirred for 16 hours. The crude product was isolated by evaporation of the solvent to yield a red oily solid. FTIR analysis of the crude reaction mixture confirmed the presence of (2,2'-bipyridyl) Ni($^{13}$CO)$_2$ [IR (THF): 1933, 1862 cm$^{-1}$ (vCO, vs)] as well as $^{13}$C-labeled polyleucine [IR (THF): 1613 cm$^{-1}$ (vAmide I, vs); 1537 cm$^{-1}$ (vAmide II, vs)]. The reaction was also run in DMF-d$_7$ (0.5 mL) under otherwise identical conditions. $^{13}$C {$^1$H} NMR (DMF-d$_7$): δ198 (s, bipyNi($^{13}$<u>C</u>O)$_2$); 177 (s, bipyNiN(H)C(H)R$^{13}$C(O)N[CH(R)$^{13}$<u>C</u>(O)NH]$_n$CH$_2$R), 174 (s, bipyNiN(H)C(H)—R$^{13}$<u>C</u>(O)N[CH(R)$^{13}$C(O)NH]$_n$CH$_2$R).

Polymerization of Glu-NCA with (2,2'-bipyridyl)Ni(COD)

In the dry box, Glu NCA (50 mg, 0.2 mmol) was dissolved in DMF (0.5 mL) and placed in a 25 mL reaction tube which could be sealed with a Teflon stopcock. An aliquot of bipyNi(COD) (50 μl of a 40 mM solution in DMF) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). $^{13}$C {$^1$H} NMR, $^1$H NMR, and FTIR spectra of this material were identical to data found for authentic samples of PBLG. H. Block, *Poly(γ-benzyl-L-glutamate) and Other Glutamic Acid Containing Polymers*, Gordon and Breach, New York, (1983). GPC of the polymer in 0.1M LiBr in DMF at 60° C.: $M_n$=22,100; $M_w/M_n$=1.15.

As discussed above, α-Amino acid-N-carboxyanhydrides (NCAs) were reacted with zerovalent nickel complexes of the type $L_2$Ni(COD) to yield metallacyclic oxidative addition products. These oxidative addition reactions were found to result in the addition across either the O—$C_5$ or the O—$C_2$ bond of the NCAs, ultimately giving, after addition of a second equivalent of NCA, chiral amido-amidate nickelacycles. The origins and structures of these complexes were elucidated by use of selectively $^{13}$C labeled NCA reagents. Stable metallacycles were obtained when L=PPh$_3$. When other donor ligands were used, the metallacycle intermediates were found to quickly react with additional NCA molecules to form polypeptides in quantitative yield and with narrow molecular weight distributions. These reactions provide a facile route to unusually stable metallacyclic amido-containing nickel intermediates.

When two equivalents of PPh$_3$ and one Ni(COD)$_2$ were reacted with one equivalent of γ-benzyl-L-glutamate-N-carboxyanydride (Glu-NCA) in THF at room temperature, rapid consumption of the NCA was observed. From the golden brown solution, an alkane soluble brown oil and a THF soluble yellow powder were isolated. Analysis of the oil confirmed the presence of (PPh$_3$)$_2$Ni(CO)$_2$ [IR(THF): ν(CO)=2000, 1939 cm$^{-1}$] which was produced by the decarbonylation of an intermediate six-membered metallacycle followed by trapping of the carbon monoxide with (PPh$_3$)$_2$Ni(COD). H. Kanazawa, et al., *Bull. Chem Soc. Jpn.*, 51:2205–2208 (1978). Infrared analysis of the yellow powder showed carbonyl stretches at 1734 and 1577 cm$^{-1}$ which were assigned, respectively, to the side-chain benzyl esters and amidate group of the chiral nickelacycle (see scheme 2 of FIG. 3).

The structures and origins of these products were elucidated when $^{13}$C$_5$-L-leucine-N-carboxyanhydride was reacted with (PPh$_3$)$_2$Ni(COD) in THF. An infrared spectrum of the crude reaction mixture showed a stretch at 1536 cm$^{-1}$ for the $^{13}$C-amidate group [$^{13}$C {$^1$H} NMR (THF-d$_8$): 182 ppm] as well as (PPh$_3$)$_2$Ni($^{13}$CO)$_2$ stretches at 1954 and 1895 cm$^{-1}$ [$^{13}$C {$^1$H} NMR (THF-d$_8$): 202 ppm] which were isotopically shifted from the unlabeled compounds (see equation 1 of FIG. 4). When $^{13}$C$_2$-L-leucine-N-carboxyanhydride was reacted with (PPh$_3$)$_2$Ni(COD) in THF, analysis of the products showed exclusive formation of (PPh$_3$)$_2$Ni($^{12}$CO)$_2$ [IR(THF): ν(CO)=2000, 1939 cm$^{-1}$] and the $^{12}$C amidate [IR(THF): ν(CO)=1580 cm$^{-1}$] (see equation 2 of FIG. 4). Since no mixed $^{13}$C/$^{12}$C products were observed, it was concluded that oxidative addition was occurring either at the $C_5$—O or the $C_2$—O bond followed by decarbonylation and addition of a second NCA molecule to yield an amido-containing nickelacycle (see scheme 2 of FIG. 3).

Figure 4:
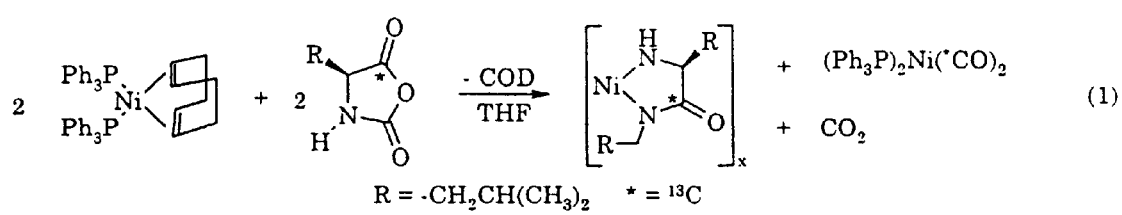
FIG. 4 shows 4 chemical reaction equations associated with amino acid derived nickelacycles, intermediates in nickel initiator mediated polypeptide synthesis.
Figure 4:
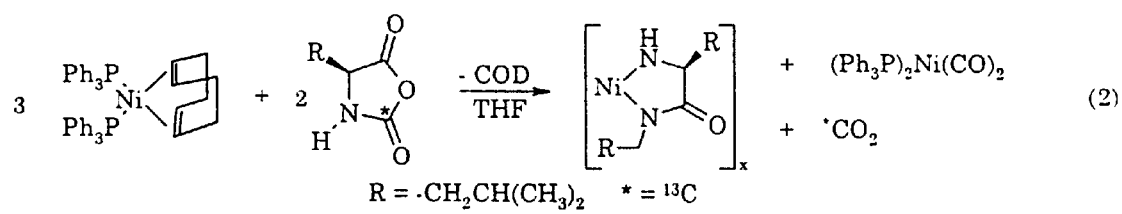
Figure 4:
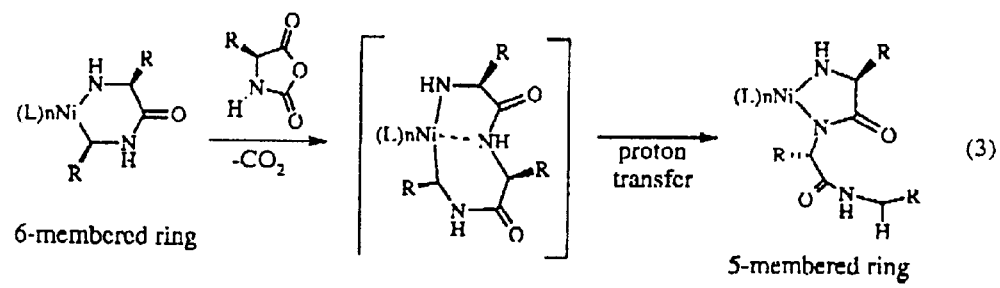
Figure 4:
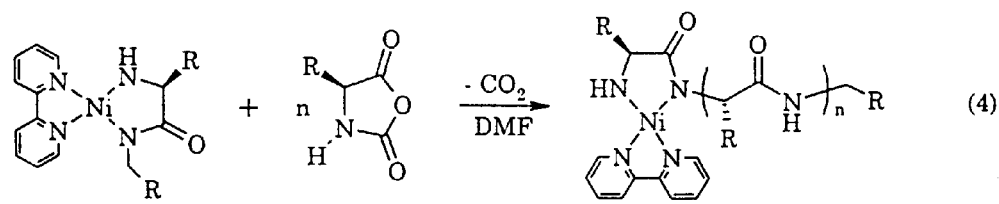

While not being bound to a specific mechanism or theory, the transformation of the initially formed 6-membered amido-alkyl nickelacycle to a 5-membered amido-amidate nickelacycle might occur through a proton-transfer mediated ring contraction induced by addition of an additional NCA monomer (see equation FIG. 4). Such a transformation has been observed for related nickel complexes.

Furthermore, quenching of polymerization reactions with DCl and HCl has shown conclusively that the nickel-alkyl bond of the 6-membered metallacycle is not present after addition of NCA molecules to the initial metallacycle, providing additional supporting evidence for the ring-contraction to the amido-amidate structure.

The structure of these metallacyclic products was further confirmed by elemental analysis and acidolysis of the complexes. The product metallacycles contain no phosphine by elemental analysis and were found to consist of the empirical formula [NiNHC(H)RC(O)NCH$_2$CHR]$_x$. Osmotic molecular weight measurements in THF (ca. 7 mg/mL) showed that the complexes aggregate as dimers. Treatment of the metallacyclic complex derived from L-leucine NCA with HCl in THF gave only a single organic product. Analysis of this product by $^1$H NMR spectroscopy and polarimetry, and comparison of the data with an authentic sample, showed it to be optically pure L-leucine isoamylamide.HCl (see scheme 2 of FIG. 3).

When the donor ligands bound to the nickel (0) precursor were varied (e.g. alkyl phosphines, α,α'-diimines), the only products isolable from stoichiometric reactions with Glu-NCA in THF were some starting nickel(0) compound and poly(g-benzyl-L-glutamate), PBLG. When 100 equivalents of Glu-NCA was added to bipyNi(COD) in DMF, all of the nickel precursor was consumed and PBLG was isolated in excellent yield (>95%) with narrow molecular weight distribution ($M_n$=22,100, $M_w/M_n$=1.15). L$_2$=donor ligand(s); COD=1,5-cyclooctadiene; bipy=2,2'-bipyridyl. It has been shown that bipyNi(COD) initiates the living polymerization of NCAs. T. J. Deming, *Nature*, 390:386–389 (1997). It was suspected that bipyNi(COD) oxidatively adds Glu-NCA to form the active polymerization initiator in situ which then rapidly consumes the remainder of the monomer. To identify this active initiator, a series of experiments were performed where bipyNi(COD) was reacted with selectively $^{13}$C labeled NCA monomers.

In order to completely consume all the bipyNi(COD) in reactions with NCAs, at least a fivefold excess of NCA monomer was used. BipyNi(COD) was reacted with five equivalents of $^{13}$C$_5$-L-leucine-N-carboxyanhydride in THF. IR and $^{13}$C {$^1$H} NMR analysis of the crude products verified the presence of bipyNi($^{13}$CO)$_2$ [IR(THF): ν($^{13}$CO)= 1933, 1862 cm$^{-1}$; $^{13}$C {$^1$H} NMR (DMF-d$_7$): 198 ppm], $^{13}$C-labeled poly-L-leucine [IR (THF): 1613 cm$^{-1}$ (vAmide I, vs); 1537 cm$^{-1}$ (vAmide II, vs); $^{13}$C {$^1$H} NMR (DMF-d$_7$): 177 ppm (bipyNiN(H)C(H)R$^{13}$C(O)N[CH(R)$^{13}$C(O)—NH]$_n$CH$_2$R)], and the labeled nickel-amidate end-group [$^{13}$C {$^1$H} NMR (DMF-d$_7$): 174 ppm (bipyNiN(H)C(H)R$^{13}$C(O)N—[CH(R)$^{13}$C(O)NH]$_n$CH$_2$R)]. The reaction with $^{13}$C$_2$-L-leucine-N-carboxyanhydride gave similar products, except for location of the $^{13}$C label. The presence of bipyNi($^{12}$CO)$_2$ [IR(THF): ν(CO)=1978, 1904 cm$^{-1}$],$^{12}$C poly-L-leucine [IR (THF): 1653 cm$^{-1}$ (vAmide I, vs); 1546 cm$^{-1}$ (vAmide II, vs)],$^{13}$ as well as the $^{12}$C-amidate end-group [IR(THF): ν(CO)=1577 cm$^{-1}$] was identified. When the reaction was run in DMF-d$_7$, the presence of liberated $^{13}$CO$_2$ was also confirmed using $^{13}$C {$^1$H} NMR [126 ppm (s, $^{13}$CO$_2$)].

All of these experiments were consistent with initial addition of the NCA to bipyNi(COD) across the $C_5$—O bond, analogous to the reactions using $(PPh_3)_2Ni(COD)$. The primary influence of the ligands manifests itself in the reactivity of the resulting products. The ligand free complex from the $PPh_3$ reaction was inert toward further reactivity with NCAs, while the bipy complex and complexes formed with other α,α'-diimines and alkyl phosphines were efficient NCA polymerization initiators. This phenomenon was directly verified by synthesis of the reactive metallacycle intermediate formed in the bipyNi(COD)/NCA reactions. The stable metallacycle (S)-[NiNHC(H)RC(O)NCH$_2$R]$_x$, R=—CH$_2$CH$_2$C(O)OCH$_2$C$_6$H$_5$) was reacted with an excess of bipy in DMF to form the ligand adduct (S)-(2,2'-bipyridyl)NiNHC(H)RC(O)NCH$_2$R, R=—CH$_2$CH$_2$C(O)OCH$_2$C$_6$H$_5$ (see scheme 2 of FIG. 3). Reaction of (S)-(2,2'-bipyridyl)NiNHC(H)RC(O)NCH$_2$R, R=—CH$_2$CH$_2$C(O)OCH$_2$C$_6$H$_5$ with 100 equivalents of Glu-NCA in DMF resulted in rapid polymer formation. The PBLG formed in this reaction was identical to that formed using bipyNi (COD) under otherwise identical conditions ($M_n$=21,600, $M_w/M_n$=1.09). The bipyNi(COD) mediated polymerizations of NCAs are therefore thought to proceed via amido-amidate nickelacycle active endgroups (see equation 4 of FIG. 4).

Example 2

Facile Synthesis of Block Copolypeptides of Defined Architecture

General Experimental Protocols and Reagents

Infrared spectra were recorded on a Perkin Elmer 1605 FTIR Spectrophotometer calibrated using polystyrene film. Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by $10^5$ Å and $10^3$ Å Phenomenex 5 μ columns using 0.1M LiBr in DMF at 60° C. as eluent. Optical rotations were measured on a Perkin Elmer Model 141 Polarimeter using a 1 mL volume cell (1 dm length). NMR spectra were measured on a Bruker AMX 500 MHz spectrometer. Chemicals were obtained from commercial suppliers and used without purification unless otherwise stated. (COD)$_2$Ni was obtained from Strem Chemical Co., and $^{13}C_1$-L-leucine and $^{13}$C-phosgene were obtained from Cambridge Isotope Labs. γ-Benzyl-L-glutamate NCA were prepared according to literature procedures. Hexanes, THF, and THF-$d_8$ were purified by distillation from sodium benzophenone ketyl. DMF and DMF-$d_7$ were purified by drying over 4 Å molecular sieves followed by vacuum distillation.

Reaction of (2,2'-bipyridyl)Ni(COD) with $^{13}C_2$-L-Leucine NCA

In the dry box, five equivalents of $^{13}C_2$-L-Leucine NCA (14.5 mg, 0.091 mmol) was added to a solution of bipyNi (COD) (5.9 mg, 0.018 mmol) in THF (1 ml). The mixture slowly turned from purple to red and was let stir for 16 hours. The crude product was isolated by evaporation of the solvent to yield a red oily solid. FTIR analysis of the crude reaction mixture confirmed the presence of (2,2'-bipyridyl) Ni(CO)$_2$ [IR (THF): 1978, 1904 cm$^{-1}$ (νCO, vs), polyleucine [IR (THF): 1653 cm$^{-1}$ (νAmide I, vs); 1546 cm$^{-1}$ (νAmide II, vs)] as well as the $^{12}$C-amidate endgroup [IR(THF): ν(CO)=1577 cm$^{-1}$]. The reaction was also run in DMF-$d_7$ (0.5 mL) under otherwise identical conditions. $^{13}$C {$^1$H} NMR (DMF-$d_7$): d 126 (s, $^{13}\underline{C}O_2$).

Reaction of (2,2'-bipyridyl)Ni(COD) with $^{13}C_5$-L-Leucine NCA

In the dry box, five equivalents of $C_5$-L-Leucine NCA (14.5 mg, 0.091 mmol) was added to a solution of bipyNi (COD) (5.9 mg, 0.018 mmol) in THF (1 ml). The mixture slowly turned from purple to red and was let stir for 16 hours. The crude product was isolated by evaporation of the solvent to yield a red oily solid. FTIR analysis of the crude reaction mixture confirmed the presence of (2,2'-bipyridyl) Ni($^{13}$CO)$_2$ [IR (THF): 1933, 1862 cm$^{-1}$ (νCO, vs)] as well as $^{13}$C-labeled polyleucine [IR (THF): 1613 cm$^{-1}$ (νAmide I, vs); 1537 cm$^{-1}$ (νAmide II, vs)]. The reaction was also run in DMF-$d_7$ (0.5 mL) under otherwise identical conditions. $^{13}$C {$^1$H} NMR (DMF-$d_7$): d 198 (s, bipyNi($^{13}\underline{C}O)_2$); 177 (s, bipyNiN(H)C(H)R$^{13}$C(O)N[CH(R)$^{13}\underline{C}$(O)—NH]$_n$CH$_2$R)), 174 (s, bipyNiN(H)C(H)R$^{13}\underline{C}$(O)N[CH(R)$^{13}$C(O)NH]$_n$CH$_2$R).

Polymerization of Glu-NCA with (2,2'-bipyridyl)Ni(COD)

In the dry box, Glu NCA (50 mg, 0.2 mmol) was dissolved in DMF (0.5 mL) and placed in a 25 mL reaction tube which could be sealed with a Teflon stopcock. An aliquot of bipyNi(COD) (50 μl of a 40 mM solution in DMF) was then added via syringe to the flask. A stirbar was added and the flask was sealed, removed from the dry box, and placed in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white stringy solid, PBLG (41 mg, 98% yield). $^{13}$C {$^1$H} NMR, $^1$H NMR, and FTIR spectra of this material were identical to data found for authentic samples of PBLG. GPC of the polymer in 0.1M LiBr in DMF at 60° C.: $M_n$=22,000; $M_w/M_n$=1.05.

As an illustrative embodiment of the invention, diblock copolymers composed of amino acid components γ-benzyl-L-glutamate and ε-carbobenzyloxy-L-lysine were synthesized. The polymers were prepared by addition of Lys-NCA to bipyNi(COD) in DMF to afford living poly(ε-carbobenzyloxy-L-lysine), PZLL, chains with organometallic end-groups capable of further chain growth. Glu-NCA was added to these polymers to yield the PBLG-PZLL block copolypeptides. The evolution of molecular weight through each stage of monomer addition was analyzed using gel permeation chromatography (GPC) and data are given in Table A below. Molecular weight was found to increase as expected upon growth of each block of copolymer while polydispersity remained low, indicative of successful copolymer formation. A. Noshay, et al., *Block Copolymers*, Academic Press, New York, (1977).

The chromatograms of the block copolypeptides showed single sharp peaks illustrating the narrow distribution of chain lengths (See FIG. 2). Copolypeptide compositions were easily adjusted by variation of monomer feed compositions, both being equivalent. Successful preparation of copolypeptides of reverse sequence (i.e. PZLL-PBLG) and of triblock structure (e.g. PBLG$_{0.39}$-b-PZLL$_{0.22}$-b-PBLG$_{0.39}$; $M_n$=256,000, $M_w/M_n$=1.15) illustrate the potential for sequence control using the nickel initiator.

Block copolymerizations were not restricted to the highly soluble polypeptides PBLG and PZLL. Copolypeptides containing L-leucine and L-proline, both of which form homopolymers which are insoluble in most organic solvents (e.g. DMF) were prepared. Data for these copolymerizations are given in Table A below. Because of the solubilizing effect of the PBLG and PZLL blocks, all of the products were soluble in the reaction media indicating the absence of any homopolymer contaminants. The block copolymers containing L-leucine were found to be strongly associating in 0.1M LiBr in DMF, a good solvent for PBLG and PZLL. Once deprotected, the assembly properties of these materials are expected to make them useful as tissue engineering scaffolds, drug carriers, and morphology-directing components in biomimetic composite formation.

TABLE A

Preparation and analysis of block copolypeptides. Polymerization initiator was bipyNi(COD) in DMF in all cases. Molecular weight ($M_n$) and polydispersity ($M_w/M_n$) were determined by tandem GPC/light scattering in 0.1M LiBr in DMF at 60° C. using dn/dc values measured in this solvent at $l_0$ = 633 mn. * First and second monomers added stepwise to the initiator; number indicates equivalents of monomer per bipyNi(COD).
Leu-NCA = L-leucine-N-carboxyanhydride.
Pro-NCA = L-proline-N-carboxyanhydride.
† Molecular weight and polydispersity after polymerization of the first monomer.
‡ Molecular weight and polydispersity of the complete block copolymer.
§ Total isolated yield of block copolymer.
‖ dn/dc = 0.123 mL/g. ¶ dn/dc = 0.108 mL/g.
dn/dc = 0.104 mL/g. ** dn/dc = 0.115 mL/g.

| First Monomer* | Second Monomer* | First Segment† | | Diblock Copolymer‡ | | yield (%)§ |
|---|---|---|---|---|---|---|
| | | $M_n$ | $M_w/M_n$ | $M_n$ | $M_w/M_n$ | |
| 52 Lys-NCA | 181 Glu-NCA | 15,000‖ | 1.12 | 66,000¶ | 1.21 | 95 |
| 90 Glu-NCA | 78 Lys-NCA | 28,500# | 1.12 | 52,700** | 1.13 | 93 |
| 104 Lys-NCA | 40 Leu-NCA | 29,500‖ | 1.13 | 34,000‖ | 1.20 | 93 |
| 182 Glu-NCA | 90 Pro-NCA | 57,600# | 1.07 | 86,000# | 1.14 | 92 |
| 120 Glu-NCA | 40 Leu-NCA | 38,000# | 1.08 | 79,000# | 1.13 | 96 |

The initiators described above were generated using bis-1,5-cyclooctadiene nickel ($Ni(COD)_2$) as the nickel source and 2,2'-bipyridyl(bipy) as the donor ligand component in tetrahydrofuran (THF) solvent. Other sources of zerovalent nickel (e.g. $Ni(CO)_4$) as well as other donor ligands (e.g. $PR_3$ [R=Me, Et, Bu, cyclohexyl, phenyl], $R_2PCH_2CH_2PR_2$ [R=Me, phenyl], α,α'-diimine ligands [1,10-phenanthroline, neocuproine], diamine ligands [tetramethylethylene diamine], and isocyanide ligands [tert-butyl isocyanide]) can be used to initiate these polymerizations. The use of other sources of zerovalent nickel (e.g. nickel-olefin complexes, nickel-carbonyl complexes, nickel-isocyanide or cyanide complexes, and nickel nitrogen or phosphorous donor ligand complexes) are possible embodiments which should not be interpreted as going beyond the concept of this invention. Likewise, the use of other donor ligands (nitrogen or phosphorous based in particular) or polymerization solvents are logical extensions of this work. Finally, other transition metals, specifically palladium, platinum, cobalt, rhodium, iridium and iron are also able to polymerize NCA monomers. The use of metals in "Group 8" (i.e. Co, Rh, Ir, Ni, Pd, Pt, Fe, Ru, Os) are thus additional potential embodiments of this invention.

Illustrative Diblock and Triblock Copolypeptides and their Synthesis

Poly(ε-benzyloxycarbonyl-L-Lysine-blocky-benzyl-γ-glutamate), PZLL-b-PBLG, Diblock Copolymer In the dry box, Glu NCA (50 mg, 0.19 mmol) was dissolved in dimethylformamide (DMF) (0.5 mL) and placed in a 25 mL reaction tube which could be sealed with a Teflon stopcock. An aliquot of (2,2'-bipyridyl)Ni(COD) (50 µl of a 40 mM solution in DMF, prepared by mixing equimolar amounts of 2,2'-bipyridyl and $Ni(COD)_2$) was then added via syringe to the flask. A stirbar was added, the flask was sealed and then stirred for 16 hours. An aliquot (50 mL) was removed from the polymerization for GPC analysis ($M_n$=28,500; $M_w/M_n$=1.12). ε-benzyloxycarbonyl-L-Lysine-N-carboxyanhydride, Lys-NCA, (50 mg, 0.16 mmol) dissolved in dimethylformamide (DMF) (0.5 mL) was then added to the reaction mixture. After stirring for an additional 16 h, polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PZLL-b-PBLG (79 mg, 93% yield). $^{13}C$ {$^1H$} NMR, $^1H$ NMR, and FTIR spectra of this material were identical to a combination of data found for authentic individual samples of PBLG and PZLL.[6] GPC of the block copolymer in 0.1M LiBr in DMF at 60° C.: $M_n$=52,700; $M_w/M_n$=1.13.

Poly(ε-benzyloxycarbonyl-L-Lysine-block-γ-benzyl-L-glutamate), PZLL-b-PBLG, Diblock Copolymer using $(PMe_3)_4Co$ In the dry box, Glu NCA (50 mg, 0.19 mmol) was dissolved in DMF (0.5 mL) and placed in a 15 mL reaction tube which could be sealed with a TEFLON™ stopper. An aliquot of $(PMe_3)_4Co$ (50 µL of a 40 mM solution in DMF:THF (1:1)) was then added via syringe to the flask. A stirbar was added, the flask was sealed and then stirred for 16 h. An aliquot (50 µL) was removed from the polymerization for GPC analysis ($M_n$=21,500; $M_w/M_n$=1.12). Lys-NCA, (50 mg, 0.16 mmol) dissolved in DMF (0.5 mL) was then added to the reaction mixture. After stirring for an additional 16 h, polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PZLL-b-PBLG (82 mg, 97% yield). $^{13}C$ {$^1H$} NMR, $^1H$ NMR, and FTIR spectra of this material were identical to a combination of data found for authentic individual samples of PBLG and PZLL. GPC of the block copolymer in 0.1M LiBr in DMF at 60° C.; $M_n$–44,700; $M_w/M_n$=1.13.

Poly(γ-benzyl-L-glutamate-block-ε-benzyloxycarbonyl-L-Lysine-block-γ-benzyl-L-glutamate) Triblock Copolymer In the dry box, Glu NCA (250 mg, 0.95 mmol) was dissolved in dimethylformamide (DMF) (1.5 mL) and placed in a 25 mL reaction tube which could be sealed with a Teflon stopcock. An aliquot of (2,2'-bipyridyl)Ni(COD) (50 µl of a 40 mM solution in DMF, prepared by mixing equimolar amounts of 2,2'-bipyridyl and $Ni(COD)_2$) was then added via syringe to the flask. A stirbar was added, the flask was sealed and then stirred for 16 hours. An aliquot (50 mL) was removed from the polymerization for GPC analysis ($M_n$=100,100; $M_w/M_n$=1.11). Lys-NCA, (125 mg, 0.42 mmol) dissolved in dimethylformamide (DMF) (0.5 mL) was then added to the reaction mixture, which was stirred for 16 h. A second aliquot (50 mL) was removed from the polymerization for GPC analysis ($M_n$=156,200; $M_w/M_n$=1.12). Finally, Glu-NCA, (250 mg, 0.95 mmol) dissolved in dimethylformamide (DMF) (1.5 mL) was then added to the reaction mixture. After stirring for an additional 16 h, polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG-b-PZLL-b-PBLG (505 mg, 96% yield). $^{13}$C $\{^1H\}$ NMR, $^1$H NMR, and FTIR spectra of this material were identical to a combination of data found for authentic individual samples of PBLG and PZLL.[6] GPC of the block copolymer in 0.1M LiBr in DMF at 60° C.: $M_n$=256,300; $M_w/M_n$=1.15.

General Preparation of Block Copolypeptides with Metal Initiators

Other diblock and triblock copolymers were prepared by a procedure identical to that described above for either PZLL-b-PBLG and PBLG-b-PZLL-b-PBLG, except that either different monomers, or different amounts of monomers, were used for the individual polymerization reactions. Examples are given in Tables 1 and 2 above. The nature of the amino acid monomer was found to be unimportant in limiting the effectiveness of these polymerizations. All amino acid NCAs tried were incorporated into block copolypeptides in any sequential order, as determined by the order of addition to the initiator. Representative monomers include, but are not limited to: the naturally occurring L-amino acids, naturally occurring D-amino acids, α-disubstituted α-amino acids, racemic α-amino acids, and synthetic α-amino acids. Block copolypeptides could be prepared using initiators other than (2,2'-bipyridyl)Ni(COD). The initiators given in Tables 4 and 5 below (except those that gave no yield of polymer) all were able to prepare block copolypeptides.

TABLE 1

Preparation and analysis of block copolypeptides.
Polymerization initiator was bipyNi(COD) in DMF in all cases. Molecular weight ($M_n$) and polydispersity ($M_w/M_n$) were determined by tandem GPC/light scattering in 0.1M LiBr in DMF at 60° C. using dn/dc values measured in this solvent at $l_0$ = 633 mn. * First and second monomers added stepwise to the initiator; number indicates equivalents of monomer per bipyNi(COD).
Leu-NCA = L-leucine-N-carboxyanhydride.
Pro-NCA = L-proline-N-carboxyanhydride.
† Molecular weight and polydispersity after polymerization of the first monomer.
‡ Molecular weight and polydispersity of the complete diblock copolymer.
§ Total isolated yield of diblock copolymer.

| First Monomer* | Second Monomer* | First Segment† $M_n$ | $M_w/M_n$ | Diblock Copolymer‡ $M_n$ | $M_w/M_n$ | yield (%)§ |
|---|---|---|---|---|---|---|
| 52 Lys-NCA | 181 Glu-NCA | 15,000 | 1.12 | 66,000 | 1.21 | 95 |
| 90 Glu-NCA | 78 Lys-NCA | 28,500 | 1.12 | 52,700 | 1.13 | 93 |
| 104 Lys-NCA | 40 Leu-NCA | 29,500 | 1.13 | 34,000 | 1.20 | 93 |
| 182 Glu-NCA | 90 Pro-NCA | 57,600 | 1.07 | 86,000 | 1.14 | 92 |
| 120 Glu-NCA | 40 Leu-NCA | 38,000 | 1.08 | 79,000 | 1.13 | 96 |

TABLE 2

Preparation and analysis of triblock copolypeptides. Polymerization initiator was bipyNi(COD) in DMF in all cases.

| Monomers and order of addition* | | | 1$^{st}$ segment† | | Diblock segment‡ | | Triblock copolymer‖ | | |
|---|---|---|---|---|---|---|---|---|---|
| 1$^{st}$ monomer | 2$^{nd}$ monomer | 3$^{rd}$ monomer | $M_n$ | $M_w/M_n$ | $M_n$ | $M_w/M_n$ | $M_n$ | $M_w/M_n$ | Yield§ |
| 450 Glu | 200 Lys | 450 Glu | 100 | 1.11 | 156 | 1.12 | 256 | 1.15 | 96 |
| 130 Glu | 120 Ala | 130 Glu | 34 | 1.07 | 47 | 1.14 | 82 | 1.20 | 94 |
| 250 Glu | 130 Leu | 250 Glu | 68 | 1.12 | 83 | 1.18 | 152 | 1.20 | 97 |
| 250 Glu | 300 Pro | 250 Glu | 67 | 1.10 | 98 | 1.17 | 167 | 1.18 | 96 |

Molecular weight ($M_n$) and polydispersity ($M_w/M_n$) were determined by tandem GPC/light scattering in 0.1M LiBr in DMF at 60° C. using dn/dc values measured in this solvent at $l_0$ = 633 nm.
*First, second and third monomers added stepwise to the initiator; number indicates equivalents of monomer per bipyNi(COD).
Lys = Lys-NCA.
Glu = Glu-NCA.
Ala = L-alanine-N-carboxyanhydride.
Leu = L-leucine-N-carboxyanhydride.
Pro = L-proline-N-carboxyanhydride.
†Molecular weight (×10$^{-3}$) and polydispersity after polymerization of the first monomer.
‡Molecular weight (×10$^{-3}$) and polydispersity after polymerization of the second monomer.
‖Molecular weight (×10$^{-3}$) and polydispersity of the complete triblock copolymer.
§Total isolated yield (%) of triblock copolymer.

Example 3

General Initiator Features; Assessment of Multiple Initiators and Effect of Chemical Structure of Efficiency: Effects of Reaction Conditions on Polymerization; and Initiator Mediated Block Copolypeptide Synthesis General Protocols and Reagents Infrared spectra were recorded on a Perkin Elmer 1605 FTIR Spectrophotometer calibrated using polystyrene film. Optical rotations were measured on a Perkin Elmer Model 141 Polarimeter using a 1 mL volume cell (1 dm length). NMR spectra and bulk magnetic susceptibility measurements (Evans method) were measured on a Bruker AMX 500 MHz spectrometer. D. F. Evans, *J. Chem. Soc.*, 2003–2009 (1959); J. K. Becconsal, *J. Mol. Phys.*, 15:129–135 (1968). C, H, N elemental analyses were performed by the Microanalytical Laboratory of the University of California, Berkeley Chemistry Department. Metal analyses were conducted using a Thermo Jarrell Ash IRIS HR ICP analyzer. Chemicals were obtained from commercial suppliers and used without purification unless otherwise stated. $(COD)_2Ni$ was obtained from Strem Chemical Co., and $^{13}C_1$-L-leucine and $^{13}C$-phosgene were obtained from Cambridge Isotope Labs. L-leucine isoamylamide hydrochloride, γ-benzyl-L-glutamate NCA and L-leucine NCA were prepared according to literature procedures. M. Bodanszky, et al., *The practice of Peptide Synthesis*, $2^{nd}$ Ed., Springer, Berlin/Heidelberg, (1994); E. R. Blout, et al., *J. Am. Chem Soc.*, 78:941–950 (1956); H. Kanazawa, et al., *Bull. Chem Soc. Jpn.*, 51:2205–2208 (1978). Hexanes, THF, and THF-$d_8$ were purified by distillation from sodium benzophenone ketyl. DMF and DMF-$d_7$ were purified by drying over 4 Å molecular sieves followed by vacuum distillation.

General Features for Formation of Active Metal Initiators

Figure 6:
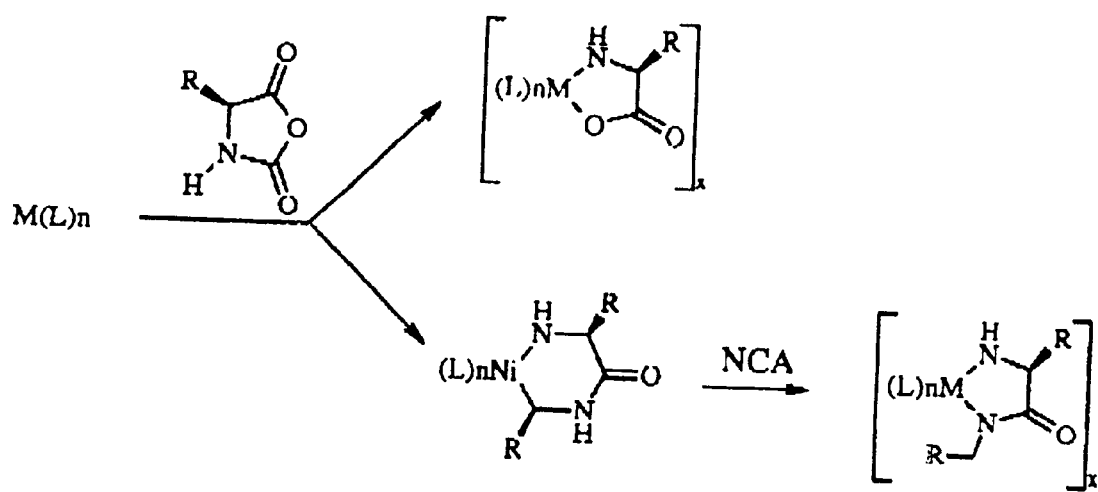
FIG. 6 shows the formation of an amido-containing metallacycle by reaction of NCAs with a metal initiator.

The efficient, controlled polymerization of NCAs using transition metal compounds requires the general formation of an amido-containing 5- or 6-membered metallacycle (FIG. 6), which is the active intermediate in the polymerizations. With regard to results described in this disclosure, these metallacycles are formed by reaction of 1 or 2 equivalents of an NCA with a metal complex, which is capable of undergoing an oxidative-addition reaction where its valence formally increases by two. A variety of NCAs can be used for this reaction (i.e. L-leucine NCA, Glu-NCA, and L-phenylalanine NCA) and there is no reason why any NCA of general structure shown in FIG. 6 would not work for this reaction. The metals which most commonly undergo two-electron oxidative-addition reactions are those in Group VIII (i.e. Fe, Ru, Os, Co, Rh, Ir, Ni, Pd, Pt) and hence these are the metals studied most extensively. Collman, J. P.; Roper, W. R. *Adv. Orgmet, Chem.*, 1968, 7, 53–94. Amido-containing metallacycles can be formed with Fe, Co, Rh, Ir and Ni, and that these complexes give controlled polymerization of NCAs. Pd and Pt complexes are also able to promote polymerization of NCAs. Virtually any low-valent transition metal (i.e. a metal in a low oxidation state) with the proper combination of electron donor ligand(s) can react with NCAs to yield amido-containing metallacyclic intermediates which could act as active polymerization initiators. Other metals which clearly fall into this category are Au, Mn, Cr, Mo, W, and V.

The range of substituents (R) which can be placed on the amido-containing metallacycles was investigated. These include the side chain functions found in amino acids themselves (e.g. $R=CH_2C_6H_5$ from phenylalanine, $R=CH_2CH(CH_3)_2$, or $R=CH_2CH_2CO_2CH_2C_6H_5$ from γ-benzylglutamate), and should thus include any organic moiety attached to an α-amino acid.

Determination of Initiator Efficiency

Efficiencies were quantified by measurement of product polymer molecular weights and molecular weight distributions, and measurement of polymerization reaction rates. Polymer molecular weights and molecular weight distributions were measured using tandem gel permeation chromatography/light scattering (GPC/LS) which was performed on a Spectra Physics Isochrom liquid chromatograph pump equipped with a Wyatt DAWN DSP light scattering detector and Wyatt Optilab DSP interoferometric refractometer. Separations were effected by $10^5$ Å and $10^3$ Å Phenomenex 5 µ columns using 0.1M LiBr in DMF eluent at 60° C. Polymerization reaction rates were obtained from kinetic data which were measured by periodically removing aliquots from a thermostated polymerization of Glu-NCA, diluting these (10-fold) with anhydrous chloroform to a known volume, and recording the intensity of the unreacted anhydride stretch at 1790 cm$^{-1}$ in the solution by FTIR spectroscopy. NCA concentrations were determined by use of an empirical calibration curve (transmittance vs. concentration) of Glu-NCA in chloroform. Plots of log (concentration) versus time gave pseudo first order polymerization rates for the different initiators.

(S)-[NiNHC(H)RC(O)NCH$_2$R]$_x$, R=—CH$_2$CH$_2$C(O) OCH$_2$C$_6$H$_5$; NiGlu$_2$

In the dry box, Glu NCA (15 mg, 0.058 mmol) was dissolved in THF (0.5 mL) and added to a stirred homogeneous mixture of PPh$_3$ (31 mg, 0.12 mmol) and (COD)$_2$Ni (16 mg, 0.058 mmol) in THF (1.5 mL). The red/brown solution was stirred for 24 hours, after which the solvent was removed in vacuo to leave a dark red oily solid. This was extracted with hexanes (3×5 mL) to yield a red/brown hexanes solution and a yellow solid. Evaporation of the hexanes solution gave a red oil containing (PPh$_3$)$_2$Ni(CO)$_2$ [IR (THF): 2000, 1939 cm$^{-1}$ (νCO, vs); 18 mg. J. Chatt, et al., *J Chem. Soc.*, 1378–1389 (1960). IR (CH$_2$ClCH$_2$Cl): 1994, 1933 cm$^{-1}$)], and drying of the solid gave the product as a yellow powder (10 mg, 75% yield). An $^1$H NMR spectrum could not be obtained in THF-$d_8$, most likely because of paramagnetism of the complex (only broad lines for the benzyl ester groups were observed). $\mu_{eff}$(THF, 293 K)=1.08$\mu_B$. Osmotic molecular weight in THF (vs. ferrocene; ca. 7 mg/mL): 910 g/mol; this corresponds to a degree of aggregation of 1.94. IR (THF): 3281 cm$^{-1}$ (νNH, s br), 1734 cm$^{-1}$ (νCO, ester, vs), 1577 cm$^{-1}$ (νCO, amidate, vs). Anal. calcd. for NiC$_{23}$H$_{26}$N$_2$O$_5$: 58.87%C, 5.59%H, 5.96%N; found: 59.07%C, 5.67%H, 5.56%N. [α]$_D^{20}$ (THF, c=0.0034)=−71.

(S)-[NiNHC(H)RC(O)NCH$_2$R]$_x$, R=—CH$_2$C$_6$H$_5$; NiPhe$_2$

In the dry box, L-phenylalanine NCA (45 mg, 0.24 mmol) was dissolved in THF (0.5 mL) and added to a stirred homogeneous mixture of PPh$_3$ (124 mg, 0.48 mmol) and (COD)$_2$Ni (64 mg, 0.24 mmol) in THF (1.5 mL). The red/brown solution was stirred for 24 hours, after which the solvent was removed in vacuo to leave a dark red oily solid. This was extracted with cold hexanes (0° C., 3×2 mL) to yield a red/brown hexanes solution and a pale orange solid. Evaporation of the hexanes solution gave a red oil containing (PPh$_3$)$_2$Ni(CO)$_2$ [IR (THF): 2000, 1939 cm$^{-1}$ (νCO, vs)], and drying of the solid gave an orange powder which could be purified by precipitation from THF/hexanes to give (S)-[NiNHC(H)RC(O)NCH$_2$R]$_x$, R=—CH$_2$C$_6$H$_5$ as a yellow powder (31 mg, 80% yield). An $^1$H NMR spectrum could not be obtained in THF-$d_8$, most likely because of paramagnetism of the complex. IR (THF): 3290 cm$^{-1}$ (νNH, s br), 1574 cm$^{-1}$ (νCO, amidate, vs). [α]$_D^{20}$ (THF, c=0.001)=−170.

(S)-(2,2'-bipyridyl)NiNHC(H)RC(O)NCH$_2$R, R=—CH$_2$CH$_2$C(O)OCH$_2$C$_6$H$_5$; (2,2'-bipyridyl)NiGlu$_2$ In the dry box, a yellow solution of NiGlu$_2$ (40 mg, 0.085 mmol) in DMF (0.5 mL) was added to a solution of 2,2'-bipyridyl (54 mg, 0.35 mmol) in DMF (0.5 mL). The homogeneous mixture was stirred for 2 d at 50° C., during which the color changed from yellow to blood red. THF (1 mL) and toluene (5 mL) were layered onto this solution resulting in precipitation of a red powder. This powder was reprecipitated from DMF/THF/toluene (1:2:10) two additional times to give (2,2'-bipyridyl)NiGlu$_2$ as a red powder (49 mg, 92% yield). An $^1$H NMR spectrum could not be obtained in THF-d$_8$, most likely because of paramagnetism of the complex (only broad lines for the benzyl ester groups were observed). IR (THF): 3281 cm$^{-1}$ (vNH, s br), 1732 cm$^{-1}$ (vCO, ester, vs), 1597 cm$^{-1}$ (vCO, amidate, vs). Anal. calcd. for NiC$_{33}$H$_{34}$N$_4$O$_5$: 63.37%C, 5.49%H, 8.95%N; found: 63.72%C, 5.49%H, 8.86%N. [α]$_D^{20}$ (THF, c=0.001)=−135.

Preparation of Other L$_2$NiGlu$_2$ and L$_2$NiPhe$_2$ Initiators

The procedures for synthesis of these compounds were identical to that described for preparation of (2,2'-bipyridyl)NiGlu$_2$ except for substitution of different ligands (L$_2$) for 2,2'-bipyridyl or the use of NiPhe$_2$ instead of NiGlu$_2$. The range of ligands included phen, LiCN, and tmeda. All of the complexes gave satisfactory analysis.

(PMe$_3$)$_2$FePhe$_2$

In the dry box, L-phenylalanine NCA (32 mg, 0.16 mmol) was dissolved in THF (0.5 mL) and added to a stirred homogeneous solution of (PMe$_3$)$_4$Fe (30 mg, 0.083 mmol) in Et$_2$O (4 mL). The pale orange solution was stirred for 24 hours, after which the resulting off-white precipitate was isolated by centrifugation. This solid was washed with Et$_2$O (3×5 mL) and then dried to give an off-white powder. The powder was purified by dissolving in THF and precipitating with hexanes (36 mg, 91%). An $^1$H NMR spectrum could not be obtained in THF-d$_8$, most likely because of paramagnetism of the complex (only broad lines for the phenyl groups were observed). IR (THF): 3296 cm$^{-1}$ (vNH, s br), 1603 cm$^{-1}$ (vCO, amidate, vs).

(tBuNC)$_2$FePhe$_2$

In the dry box, (PMe$_3$)$_2$FePhe$_2$ (20 mg, 0.042 mmol) was dissolved in THF (2 mL) and mixed with tBuNC (24 mL, 0.252 mmol) in THF (2 mL). The solution was stirred overnight during which it slowly turned from brown to yellow. The product was isolated by repeated precipitation of a yellow powder from THF by addition to hexanes. Drying gave a yellow solid (19 mg, 94%). IR (THF): 3289 cm$^{-1}$ (vNH, s br), 2150 cm$^{-1}$ (vNC, tBuNC, vs), 1626 cm$^{-1}$ (vCO, amidate, vs).

(2,2'-bipyridyl)FePhe$_2$

In the dry box, (PMe$_3$)$_2$FePhe$_2$ (20 mg, 0.042 mmol) was dissolved in THF (2 mL) and mixed with tBuNC (33 mg, 0.168 mmol) in THF (2 mL). The solution was stirred overnight during which it slowly turned from brown to deep red. The product was isolated by repeated precipitation of a red powder from DMF:THF (1:1) by addition to hexanes. Drying gave a red solid (18 mg, 89%). IR (THF): 3291 cm$^{-1}$ (vNH, s br), 1600 cm$^{-1}$ (vCO, amidate, vs).

Polymerization of Glu-NCA with (2,2'-bipyridyl)Ni(COD)

In the dry box, Glu NCA (50 mg, 0.2 mmol) was dissolved in tetrahydrofuran (THF) (0.5 mL) and placed in a 25 mL reaction tube which could be sealed with a Teflon stopcock. An aliquot of (2,2'-bipyridyl)Ni(COD) (50 μl of a 40 mM solution in THF, prepared by mixing equimolar amounts of 2,2'-bipyridyl and Ni(COD)$_2$) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). $^{13}$C {$^1$H} NMR, $^1$H NMR, and FTIR spectra of this material were identical to data found for authentic samples of PBLG. H. Block, *Poly(g-benzyl-L-glutamate) and Other Glutamic Acid Containing Polymers*, Gordon and Breach, New York, (1983). GPC of the polymer in 0.1M LiBr in DMF at 60° C.: M$_n$=98,100; M$_w$/M$_n$=1.15.

General Polymerization of Glu-NCA with (2.2'-bipyridyl)Ni(COD) in Different Solvents The procedure followed was identical to that used for the (2,2'-bipyridyl)Ni(COD) in THF except for substitution of different solvents for THF. The range of other solvents included: toluene, dioxane, acetonitrile, ethyl acetate, and DMF. The results of these polymerizations are given in Table 3 below. The initiator efficiencies were determined by analysis of polymer yields, proximity of the found molecular weights to the theoretical values, and the narrowness of the molecular weight distributions.

TABLE 3

Effect of solvent on polymerizations of Glu-NCA using 2,2'-bipyridylNi(COD) initiator. Moles monomer:moles initiator = 180:1.
All polymerizations were run at 20° C.
for 16 hours under nitrogen atmosphere.

| Notebook # | Solvent | Yield (%) | M$_n$ | M$_w$/M$_n$ |
|---|---|---|---|---|
| 3-23 | Ethyl acetate | 99 | 109,000 | 1.12 |
| 2-148 | Toluene | 97 | 146,000 | 1.11 |
| 3-23 | Dioxane | 96 | 126,000 | 1.20 |
| 3-23 | Acetonitrile | 62 | 75,000 | 1.45 |
| 2-144 | THF | 96 | 142,000 | 1.05 |
| 2-151 | DMF | 97 | 40,000 | 1.19 |

General Polymerization of Glu-NCA with (L$_2$)Ni(COD) Initiators

Figure 5:
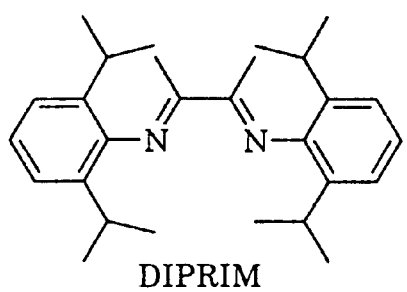
FIG. 5 shows chemical structures of some ligands used in NCA polymerization reactions
Figure 5:
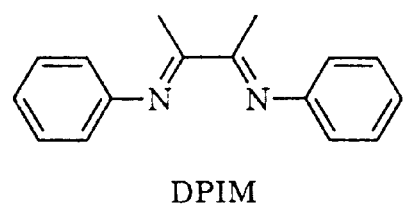
Figure 5:
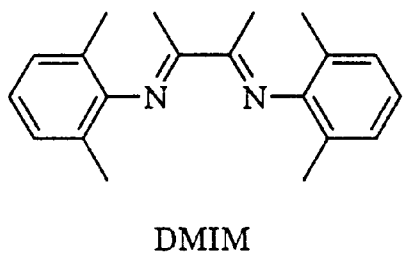
Figure 5:
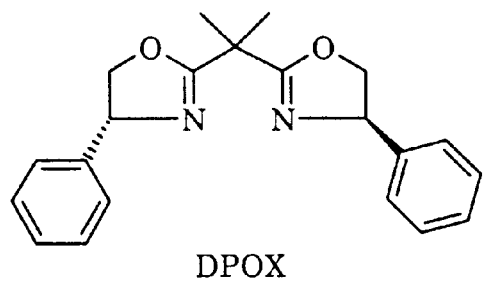
Figure 5:
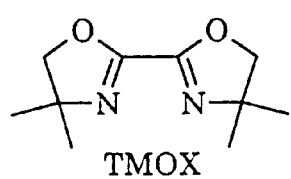
Figure 5:
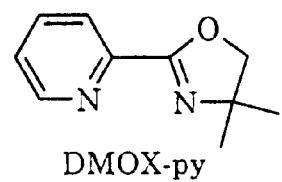

The procedure followed was identical to that used for the (2,2'-bipyridyl)Ni(COD) initiator except for substitution of different ligand molecules (L$_2$) for 2,2'-bipyridyl. The range of ligands (L$_2$) included: tricyclohexylphosphine (PCy$_3$, 1 and 2 equivalents per metal), tert-butyl isocyanide (tBuNC, 2 and 4 equivalents), lithium cyanide (2 equivalents), trimethylphosphine (PMe$_3$, 2 equivalents), triethylphosphine (PEt$_3$, 2 equivalents), tributylphosphine (PBu$_3$, 2 equivalents), triphenylphosphine (PPh$_3$, 1 and 2 equivalents), 1,2-bis(diphenylphosphino)ethane (DIPHOS), 1,2-bis(dimethylphosphino)ethane (dmpe), tetramethylethylenediamine (tmeda), (−)-sparteine, 1,10-phenanthroline (phen), neocuproine (ncp), as well as the compounds shown in FIG. 5. The results of these polymerizations are given in Table 4 below. The initiator efficiencies were determined by analysis of polymer yields, proximity of the found molecular weights to the theoretical values, and the narrowness of the molecular weight distributions.

TABLE 4

Effect of Ligands on L$_2$Ni(COD) initiators for polymerizations of Glu-NCA.
[M]:[I] = moles monomer:moles initiator.
All polymerizations were run at 20° C.
for 16 hours under nitrogen atmosphere.
L$_2$:Ni(COD)$_2$ = 1:1
unless specified otherwise.

| Notebook # | Ligand (L$_2$) | [M]:[I] | Solvent | Yield (%) | M$_n$ × 10$^{-3}$ | M$_w$/M$_n$ |
|---|---|---|---|---|---|---|
| 2-144 | 2,2'-bipyridyl | 180 | THF | 96 | 142 | 1.05 |
| 2-148 | DIPRIM | " | " | 60 | 165 | 1.21 |
| 2-148 | dmpe | " | " | 90 | 275 | 1.04 |
| 2-148 | COD | " | " | 0 | — | — |
| 2-151 | DMIM | " | " | 0 | — | — |
| 2-151 | 2 PPh$_3$ | " | " | 0 | — | — |
| 2-151 | 1 PPh$_3$ | " | " | 78 | 126 | 1.26 |
| 2-151 | phen | 90 | " | 94 | 151 | 1.15 |
| 2-151 | ncp | " | " | 94 | 293 | 1.17 |
| 3-2 | DPIM | " | " | 0 | — | — |
| 3-2 | DPOX | " | " | 96 | 189 | 1.06 |
| 3-2 | 2 PMe$_3$ | " | " | 94 | 244 | 1.16 |
| 3-10 | tmeda | " | " | 96 | 305 | 1.09 |

TABLE 4-continued

Effect of Ligands on L₂Ni(COD)
initiators for polymerizations of Glu-NCA.
[M]:[I] = moles monomer:moles initiator.
All polymerizations were run at 20° C.
for 16 hours under nitrogen atmosphere.
$L_2:Ni(COD)_2 = 1:1$
unless specified otherwise.

| Notebook # | Ligand ($L_2$) | [M]:[I] | Solvent | Yield (%) | $M_n \times 10^{-3}$ | $M_w/M_n$ |
|---|---|---|---|---|---|---|
| 3-11 | DIPHOS | " | " | 0 | — | — |
| 3-21 | 2 $PCy_3$ | " | " | 0 | — | — |
| 3-21 | 1 $PCy_3$ | " | " | 0 | — | — |
| 3-34 | 2 t-BuNC | " | " | 76 | 218 | 1.09 |
| 3-34 | 4 t-BuNC | " | " | 74 | 190 | 1.15 |
| 3-37 | 2 $PEt_3$ | " | " | 92 | 251 | 1.08 |
| 3-37 | 2 $PBu_3$ | " | " | 88 | 196 | 1.14 |
| JJ-Rep | (−) sparteine | 200 | " | 92 | 174 | 1.05 |
| JJ-Rep | TMOX | " | " | 98 | 170 | 1.14 |
| JJ-Rep | DMOX-py | " | " | 90 | 157 | 1.03 |
| 2-151 | 2,2'-bipyridyl | 152 | DMF | 97 | 35 | 1.14 |
| 3-11 | tmeda | 90 | " | 96 | 87 | 1.36 |
| 3-11 | dmpe | " | " | 96 | 60 | 1.33 |
| 3-11 | phen | " | " | 98 | 41 | 1.21 |
| 3-11 | ncp | " | " | 99 | 48 | 1.45 |
| 3-11 | DIPHOS | " | " | 94 | 100 | 1.50 |
| 3-21 | 1 $PCy_3$ | " | " | 35 | 46 | 1.18 |

General Polymerization of Glu-NCA with Other Transition Metal Initiators

The procedure followed was identical to that used for the (2,2'-bipyridyl)Ni(COD) initiator except for substitution of different metal complexes for (2,2'-bipyridyl)Ni(COD). The range of metal complexes included: (2,2'-bipyridyl)Ni(CO)₂; (S)-[NiNHC(H)RC(O)NCH₂R]ₓ, R=—CH₂CH₂C(O)OCH₂C₆H₅ (NiGlu₂); (S)-(2,2'-bipyridyl)NiNHC(H)RC(O)NCH₂R, R=—CH₂CH₂C(O)OCH₂C₆H₅ (2,2'-bipyridylNiGlu₂); (S)-Li₂(CN)₂NiNHC(H)RC(O)NCH₂R, R=—CH₂CH₂C(O)OCH₂C₆H₅ (Li₂(CN)₂NiGlu₂); (S)-(phen)NiNHC(H)RC(O)NCH₂R, R=—CH₂CH₂C(O)OCH₂C₆H₅ (phenNiGlu₂); (S)-(phen)NiNHC(H)RC(O)NCH₂R, R=—CH₂C₆H₅ (phenNiPhe₂); (S)-(tmeda)NiNHC(H)RC(O)NCH₂R, R=—CH₂C₆H₅ (tmedaNiPhe₂); dmpeCoPhe₂; (PMe₃)₂CoPhe₂; (PMe₃)₄Co; dmpeRhCl; dmpeIrCl; h⁵—C₅H₅Co(CO)₂ (CpCo(CO)₂); (2,2'-bipyridyl)Co(CO)₂)₂; ((PPh₃)₂Co(CO)₂)₂; (PMe₃)₄Fe; (2,2'-bipyridyl)₂Fe; (S)-(PMe₃)₂FeNHC(H)RC(O)NCH₂R, R=—CH₂C₆H₅ ((PMe₃)₂FePhe₂); (S)-(tBuNC)₂FeNHC(H)RC(O)NCH₂R, R=—CH₂C₆H₅ ((tBuNC)₂FePhe₂); (S)-(2,2'-bipyridyl)FeNHC(H)RC(O)NCH₂R, R=—CH₂C₆H₅ ((2,2'-bipyridyl)FePhe₂); (PPh₃)₄Pd; tris(dibenzylideneacetone)dipalladium (Pd₂(DBA)₃) plus 4 equivalents of PEt₃; (PEt₃)₂Pt(COD); and (dmpe)₂Co. The results of these polymerizations are given in Table 5 below. The initiator efficiencies were determined by analysis of polymer yields, proximity of the found molecular weights to the theoretical values, and the narrowness of the molecular weight distributions.

Polymerization of Glu-NCA with (PMe₃)₄Co

In the dry box, Glu NCA (50 mg, 0.2 mmol) was dissolved in DMF (0.5 mL) and placed in a 15 mL reaction tube which could be sealed with a TEFLON™ stopper. An aliquot of (PMe₃)₄Co (50 µL of a 40 mM solution in DMF:THF (1:1)) was then added via syringe to the flask. A stirbar was added and the flask was sealed, removed from the dry box, and stirred in a thermostated 25° C. bath for 16 h. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (42 mg, 99% yield). ¹³C {¹H} NMR, ¹H NMR, and FTIR spectra of this material were identical to data found for authentic samples of PBLG. GPC of the polymer in 0.1M LiBr in DMF at 60° C.: $M_n$=21,600; $M_w/M_n$=1.11.

(S)-[CoNHC(H)RC(O)NCH₂R]₂₅ R=CH₂C₆H₆; CoPhe₂

In the dry box, Phe NCA (9.0 mg, 0.046 mmol) was dissolved in THF (0.5 mL) and added to a stirred homogeneous solution of (PPh₃)₃Co(N₂) (40 mg, 0.046 mmol) in THF (1.5 mL). The red/brown solution was stirred for 24 h, after which the solvent was removed in vacuo to leave a red/orange oily solid. This was extracted with hexanes (3×5 mL) to yield an orange hexanes solution and a tan solid. Evaporation of the hexanes solution gave a brown oil containing [(PPh₃)₃Co(CO)]₂ [IR (THF): 1909, 1875 cm⁻¹ (νCO, vs); 15 mg; Literature: IR (KBr): 1904, 1877 cm⁻¹)], and drying of the solid gave the product as a tan powder (11 mg, 74% yield). An ¹H NMR spectrum could not be obtained in THF-d₈ most likely because of paramagnetism of the complex (only broad lines for the phenyl rings were observed). IR (THF): 3310 cm⁻¹ (νNH, s br), 1600 cm⁻¹ (νCO, amidate, vs).

(S)-(dmpe)CoNHC(H)RC(O)NCH₂R, R=—CH₂C₆H₆ dmpeCoPhe₂

In the dry box, a light brown solution of 1 (40 mg, 0.12 mmol) in DMF (0.5 mL) was added to a solution of bis(dimethylphosphino)ethane, dmpe, (35 µL, 0.21 mmol) in DMF (0.5 mL). The homogeneous mixture was stirred for 2 d at 50° C., during which the color changed from yellow to orange/red. THF (1 mL) and toluene (5 mL) were layered onto this solution resulting in separation of a brown oil. This oil was isolated from DMF/THF/toluene (1:2:10) two additional times to give the product (49 mg, 86% yield). An ¹H NMR spectrum could not be obtained in THF-d₈, most likely because of paramagnetism of the complex (only broad lines for the phenyl and methyl groups were observed). IR (THF): 3295 cm⁻¹ (νN11, s br), 1603 cm⁻¹ (νCO, amidate, vs).

Polymerization of Glu-NCA Using dmpeCoPhe₂

In the dry box, Glu NCA (50 mg, 0.2 mmol) was dissolved in DMF (0.5 mL) and placed in a 15 mL reaction tube which could be sealed with a TEFLON™ stopper. An aliquot of dmpeCoPhe₂ (50 µL of a 40 mM solution in DMF) was then added via syringe to the flask. A stirbar was added and the flask was sealed, removed from the dry box, and stirred in a thermostated 25° C. bath for 16 h. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). ¹³C {¹H} NMR, ¹H NMR, and FTIR spectra of this material were identical to data found for authentic samples of PBLG. GPC of the polymer in 0.1M LiBr in DMF at 60° C.: $M_n$=20,900: $M_w/M_n$=1.07.

TABLE 5

Efficiency of different transition metal
initiators for polymerization of Glu-NCA.
[M]:[I] = moles monomer:moles initiator.
All polymerizations were run at 20° C.
for 16 hours under nitrogen atmosphere.

| Notebook # | Metal complex | [M]:[I] | Solvent | Yield (%) | $M_n \times 10^{-3}$ | $M_w/M_n$ |
|---|---|---|---|---|---|---|
| 3-40 | 2,2'-bipyridyl-Ni(CO)₂ | 50 | THF | 54 | 38 | 1.38 |
| 3-45 | NiGlu₂ | " | DMF | 84 | 35 | 1.26 |
| 3-34 | 2,2'-bipyridyl-NiGlu₂ | " | THF | 97 | 142 | 1.12 |
| 3-58 | Li₂(CN)₂NiGlu₂ | " | " | 96 | 100 | 1.27 |

TABLE 5-continued

Efficiency of different transition metal
initiators for polymerization of Glu-NCA.
[M]:[I] = moles monomer:moles initiator.
All polymerizations were run at 20° C.
for 16 hours under nitrogen atmosphere.

| Notebook # | Metal complex | [M]:[I] | Solvent | Yield (%) | $M_n \times 10^{-3}$ | $M_w/M_n$ |
|---|---|---|---|---|---|---|
| 3-64 | phenNiGlu$_2$ | 30 | " | 97 | 83 | 1.15 |
| " | phenNiPhe$_2$ | " | " | 98 | 98 | 1.11 |
| 3-62 | tmedaNiPhe$_2$ | " | " | 96 | 100 | 1.10 |
| 3-61 | 2,2'-bipyridyl NiGlu$_2$ | 90 | DMF | 94 | 60 | 1.18 |
| 3-64 | phenNiGlu$_2$ | " | " | 97 | 36 | 1.15 |
| 3-68 | phenNiPhe$_2$ | " | CH$_2$Cl$_2$ | 93 | 86 | 1.09 |
| 3-58 | CpCo(CO)$_2$ | " | THF | 0 | — | — |
| 3-36 | (2,2'-bipyridyl-Co(CO)$_2$)$_2$ | " | " | 0 | — | — |
| 3-36 | ((PPh$_3$)$_2$ Co(CO)$_2$)$_2$ | " | " | 0 | — | — |
| 3-73 | (dmpe)$_2$Co | 50 | " | 97 | 80 | 1.09 |
| AG-Rep | (PPh$_3$)$_4$Pd | 150 | " | 82 | 220 | 1.05 |
| AG-Rep | Pd$_2$(DBA)$_3$ + 4 PEt$_3$ | 150 | " | 81 | 254 | 1.06 |
| AG-Rep | (PEt$_3$)$_2$Pt(COD) | 150 | " | 84 | 236 | 1.04 |
| 3-61 | (2,2'-bipyridyl)$_2$Fe | 90 | " | 80 | 50 | 1.10 |
| 3-68 | (PMe$_3$)$_4$Fe | 50 | " | 0 | — | — |
| 3-69 | (PMe$_3$)$_2$FePhe$_2$ | 90 | " | 0 | — | — |
| 3-75 | (t-BuNC)$_2$FePhe$_2$ | 50 | " | 96 | 84 | 1.11 |
| 3-75 | (PMe$_3$)$_2$-FePhe$_2$ | 90 | DMF | 50 | 25 | 1.21 |
| 3-75 | (2,2'-bipyridyl)-FePhe$_2$ | " | " | 97 | 36 | 1.18 |
| 3-75 | (t-BuNC)$_2$FePhe$_2$ | " | " | 96 | 38 | 1.15 |
| 3-127 | (PMe$_3$)$_4$Co | 100 | DMF | 97 | 22 | 1.11 |
| 3-124 | (PMe$_3$)$_4$Co | 50 | THF | 98 | 47 | 1.17 |
| 3-117 | dmpeIrCl | 25 | THF | 97 | 67 | 1.28 |
| 3-117 | (PMe$_3$)IrCl | 25 | THF | 96 | 89 | 1.14 |
| 3-112 | (PEt$_3$)$_2$IrCl | 50 | THF | 25 | 50 | 1.40 |
| 3-113 | (CH$_2$(PEt$_2$)$_2$)$_2$-IrCl | 50 | THF | 97 | 122 | 1.21 |
| 3-114 | (CH$_2$(PCy$_2$)$_2$)$_2$-IrCl | 50 | THF | 94 | 188 | 1.17 |
| 3-118 | dmpeRhCl | 50 | THF | 98 | 99 | 1.16 |
| 3-118 | (PMe$_3$)$_2$RhCl | 50 | THF | 39 | 238 | 1.22 |
| 3-103 | dmpeCoPhe$_2$ | 100 | DMF | 98 | 21 | 1.07 |

What is claimed is:

1. A method of making a mixture containing a solvent and a block copolypeptide comprising:

(a) reacting a first amino acid N-carboxyanhydride (NCA) monomer with an initiator complex in a suitable solvent, said complex comprising a low valent transition metal and a Lewis Base donor ligand, for a time and under conditions effective to exhaust the first monomer and to generate a mixture containing a polyamino acid chain bearing an amido-containing metallacycle end group and the solvent; and (b) reacting a second amino acid NCA monomer with the polyamino acid chain of step (a), wherein the second monomer is different from the first monomer, for a time and under conditions effective to exhaust the second monomer and to generate a mixture containing a block copolypeptide and the solvent.

2. The method of claim 1, wherein the initiator complex reacts with the first amino acid NCA monomer to form an amido-containing metallacycle intermediate of the formula:

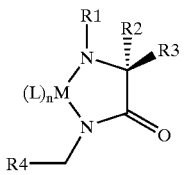

wherein

M is a transition metal;

L is the Lewis Base donor ligand;

n is an integer from 1 to 4 enumerating the donor ligands per metal atom

R1, R2 and R3 are hydrogen or a side chain of an amino acids consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine; and R4 is a side chain of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

3. The method of claim 2, wherein M is selected from the group consisting of nickel, palladium, platinum, cobalt, rhodium, iridium and iron.

4. The method of claim 2, wherein the Lewis Base donor ligand is selected from the group consisting of a pyridyl ligand, a diimine ligand, a bisoxazoline ligand, an alkyl phosphine ligand, an aryl phosphine ligand, a tertiary amine ligand, an isocyanide ligand, a cyanide ligand and a nitrile ligand.

5. The method of claim 2, wherein R1 and either R2 or R3 are hydrogen.

6. The method of claim 1, wherein the first amino acid NCA monomer is the NCA monomer of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

7. The method of claim 1, step (a) beginning with a ratio of one to 450 molar equivalents of the first monomer per mole of initiator complex.

8. The method of claim 1, step (b) beginning with a ratio of one to 450 molar equivalents of the second monomer per mole of initiator complex present at the beginning of step (a).

9. A method of making a composition containing a solvent and a polypeptide having segregated domains of mixed monomers comprising:

(a) reacting a first mixture of amino acid N-carboxyanhydride (NCA) monomers with an initiator complex in a suitable solvent, said complex comprising a low valent transition metal and a Lewis Base donor ligand, for a time and under conditions effective to exhaust the first mixture of monomers and to generate a composition containing the solvent and a polyaminoacid chain bearing an amido-containing metallacycle end group; and (b) reacting a second mixture of NCA monomers with the polyaminoacid chain, wherein the second mixture has a different composition of NCA monomers than the first mixture, for a time and under conditions effective to exhaust the second mixture of NCA monomers and to generate a composition containing the solvent and a polypeptide having segregated domains of mixed monomers.

10. The method of claim 9, wherein the initiator complex reacts with the first mixture of aminoacid-N-carboxyanhydride monomers to form an amido-containing metallacycle intermediate of the formula:

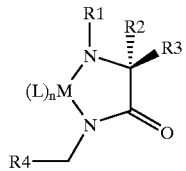

wherein

M is a transition metal;

L is the Lewis Base donor ligand;

n is an integer from 1 to 4 enumerating the donor ligands per metal atom;

R1, R2 and R3 are hydrogen or a side chain of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine; and R4 is a side chain of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

11. A method of making a composition containing a solvent and a polypeptide having segregated domains of mixed monomers comprising:

(a) reacting a first mixture of amino acid N-carboxyanhydride (NCA) monomers with an initiator complex in a suitable solvent, said complex comprising a low valent transition metal and a Lewis Base donor ligand, for a time and under conditions effective to exhaust the first mixture of monomers and to generate a composition containing the solvent and a polyaminoacid chain bearing an amido-containing metallacycle end group;

(b) reacting a second mixture of NCA monomers with the polyaminoacid chain, wherein the second mixture has a different composition of NCA monomers than the first mixture, for a time and under conditions effective to exhaust the second mixture of NCA monomers and to generate a composition containing the solvent and a polypeptide having segregated domains of mixed monomers; and (c) reacting at least one additional mixture of amino acid NCA monomers with the composition containing the polypeptide generated in (b), wherein the additional mixture has a different composition of NCA monomers than the second mixture, each NCA monomer containing an amino acid residue, for a time and under conditions effective to exhaust the additional mixture of NCA monomers and to add the amino acid residues from the additional mixture of monomers to the polypeptide contained in the composition.

12. The method of claim 10, wherein R1 and either R2 or R3 are hydrogen.

13. A method of adding an amino acid residue to a polyaminoacid chain comprising reacting a polyaminoacid chain bearing an amido-containing metallacycle end group with one or more amino acid N-carboxyanhydride (NCA) monomers in a suitable solvent, each monomer containing an amino acid residue, for a time and under conditions effective to add the amino acid residue to the polyaminoacid chain.

14. The method of claim 13, wherein the polyaminoacid chain bearing an amido-containing metallacycle end group is of the formula:

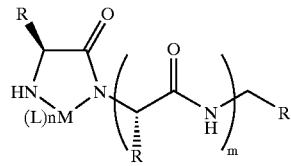

wherein

M is a transition metal;

L is a Lewis Base donor ligand;

n is an integer from 1 to 4 enumerating the donor ligands per metal atom;

R is a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and m is an integer greater than one.

15. The method of claim 14, wherein M is a transition metal selected from the group consisting of nickel, palladium, platinum, cobalt, rhodium, iridium and iron.

16. The method of claim 14, wherein the Lewis Base donor ligand is selected from the group consisting of a pyridyl ligand, a diimine ligand, a bisoxazoline ligand, an alkyl phosphine ligand, an aryl phosphine ligand, a tertiary amine ligand, an isocyanide ligand, a cyanide ligand and a nitrile ligand.

17. The method of claim 13, wherein the NCA monomer contains an amino acid residue selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

18. A method of making a mixture containing a solvent and an amido-containing metallacycle comprising reacting an amino acid N-carboxyanhydride (NCA) monomer with an initiator complex in a suitable solvent, said complex comprising a low valent transition metal and a Lewis Base donor ligand, for a time under conditions effective to form a mixture comprising an amido-containing metallacycle and the solvent.

19. The method of claim 18, said amido-containing metallacycle having formula I, II, or III:

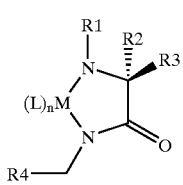

I

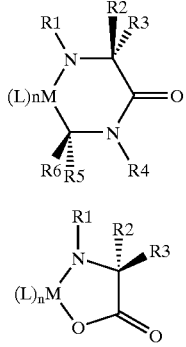

wherein
- M is a transition metal;
- L is the Lewis Base donor ligand;
- n is an integer from 1 to 4 enumerating the donor ligands per metal atom;
- R1, R2, R3, R5 and R6 are hydrogen or a side chain of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine;
- R4 of formula II is hydrogen; and
- R4 of formula I is a side chain of an amino acid selected from the group consisting of alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

20. The method of claim 19, wherein R1 and either R2 or R3 are hydrogen.

21. The method of claim 20, the metallacycle having formula II, wherein either R5 or R6 is hydrogen.

22. A method of making a block copolypeptide comprising:
  (a) reacting a first amino acid N-carboxyanhydride (NCA) monomer with an initiator complex in a suitable solvent, said complex comprising a low valent transition metal and a Lewis Base donor ligand, for a time and under conditions effective to exhaust the first monomer and to generate a composition containing a polyamino acid chain bearing an amido-containing metallacycle end group and the solvent;
  (b) reacting a second amino acid NCA monomer with the composition containing the polyamino acid chain of step (a), wherein the second monomer is different from the first monomer, for a time and under conditions effective to exhaust the second monomer and to generate a composition containing a block copolypeptide and the solvent; and
  (c) isolating the block copolypeptide.

23. A method of making a polypeptide having segregated domains of mixed monomers comprising:
  (a) reacting a first mixture of amino acid N-carboxyanhydride (NCA) monomers with an initiator complex in a suitable solvent, said complex comprising a low valent transition metal and a Lewis Base donor ligand, for a time and under conditions effective to exhaust the first mixture of monomers and to generate a composition containing the solvent and a polyaminoacid chain bearing an amido-containing metallacycle end group;
  (b) reacting a second mixture of NCA monomers with the composition containing the polyaminoacid chain, wherein the second mixture has a different composition of NCA monomers than the first mixture, for a time and under conditions effective to exhaust the second mixture of NCA monomers and to generate a composition containing the solvent and a polypeptide having segregated domains of mixed monomers; and
  (c) isolating the polypeptide.

24. A method of making an amido-containing metallacycle comprising:
  (a) reacting an amino acid N-carboxyanhydride (NCA) monomer with an initiator complex in a suitable solvent, said complex comprising a low valent transition metal and a Lewis Base donor ligand, for a time under conditions effective to form a composition containing an amido-containing metallacycle and the solvent; and
  (b) isolating the metallacycle.

25. A method of making a triblock copolypeptide comprising:
  (a) reacting a first amino acid N-carboxyanhydride (NCA) monomer with an initiator complex in a suitable solvent, said complex comprising a low valent transition metal and a Lewis Base donor ligand, for a time and under conditions effective to exhaust the first monomer and to generate a composition containing the solvent and a polyamino acid chain bearing an amido-containing metallacycle end group;
  (b) reacting a second amino acid NCA monomer with the composition containing the polyamino acid chain of step (a), wherein the second monomer is different from the first monomer, for a time and under conditions effective to exhaust the second monomer and to generate a composition containing the solvent and a diblock copolypeptide;
  (c) reacting a third amino acid NCA monomer with the composition containing the diblock copolypeptide of step (b), wherein the third monomer is different from the second monomer, for a time and under conditions effective to exhaust the second monomer and to generate a composition containing the solvent and a triblock copolypeptide; and
  (d) recovering the triblock copolypeptide.

* * * * *